US009782560B2

(12) United States Patent
Schaeffer

(10) Patent No.: US 9,782,560 B2
(45) Date of Patent: *Oct. 10, 2017

(54) SHORT WIRE CABLE CATHETER

(71) Applicant: Cook Medical Technologies LLC, Bloomington, IN (US)

(72) Inventor: Darin G. Schaeffer, Bloomington, IN (US)

(73) Assignee: COOK MEDICAL TECHNOLOGIES, LLC., Bloomington, IN (US)

( * ) Notice: Subject to any disclaimer, the term of this patent is extended or adjusted under 35 U.S.C. 154(b) by 593 days.

This patent is subject to a terminal disclaimer.

(21) Appl. No.: 14/196,374

(22) Filed: Mar. 4, 2014

(65) Prior Publication Data

US 2014/0188044 A1 Jul. 3, 2014
US 2016/0228680 A9 Aug. 11, 2016

Related U.S. Application Data

(63) Continuation of application No. 13/498,373, filed as application No. PCT/US2010/049758 on Sep. 22, 2010, now Pat. No. 8,758,295.
(Continued)

(51) Int. Cl.
*A61M 25/10* (2013.01)
*A61M 25/00* (2006.01)
(Continued)

(52) U.S. Cl.
CPC .... *A61M 25/0045* (2013.01); *A61M 25/0043* (2013.01); *A61M 25/10* (2013.01);
(Continued)

(58) Field of Classification Search
CPC .......... A61M 25/0045; A61M 25/0043; A61M 25/10; A61M 2025/1093;
(Continued)

(56) References Cited

U.S. PATENT DOCUMENTS 4,898,591 A   2/1990   Jang et al.
4,960,410 A * 10/1990 Pinchuk ............ A61M 25/0054
                                                604/103.1
(Continued)

FOREIGN PATENT DOCUMENTS

WO    WO 2006/107919 A1    10/2006

OTHER PUBLICATIONS

Extended European Search Report for European Application No. 12193909.4, dated May 15, 2013, 17 pages.
(Continued)

*Primary Examiner* — Imani Hayman
*Assistant Examiner* — Jenna Zhang
(74) *Attorney, Agent, or Firm* — Brinks Gilson & Lione

(57) ABSTRACT

A balloon catheter device of the present invention includes an elongate catheter shaft comprising multifilar cable tubing having a proximal portion and a distal portion. The proximal portion includes a coating that allows the shaft to provide a patent fluid passage, and a part of the distal portion inside a balloon may be uncoated or otherwise open to the balloon lumen, allowing for passage of fluid through the shaft into the balloon lumen. The distal cable tube end includes a connection structure configured to provide desirable strength, pushability, and trackability.

15 Claims, 27 Drawing Sheets

Related U.S. Application Data

(60) Provisional application No. 61/247,175, filed on Sep. 30, 2009, provisional application No. 61/367,534, filed on Jul. 26, 2010.

(51) Int. Cl.
*A61M 29/00* (2006.01)
*A61M 25/01* (2006.01)

(52) U.S. Cl.
CPC ............. *A61M 2025/0183* (2013.01); *A61M 2025/1093* (2013.01)

(58) Field of Classification Search
CPC ...... A61M 2025/0183; A61M 25/0029; A61M 25/0023; A61M 25/0052; A61M 25/0662
See application file for complete search history.

(56) References Cited

U.S. PATENT DOCUMENTS

| | | | | |
|---|---|---|---|---|
| 5,695,468 A | * | 12/1997 | Lafontaine | A61M 25/1018 604/96.01 |
| 5,702,439 A | * | 12/1997 | Keith | A61M 25/0662 604/524 |
| 6,548,010 B1 | * | 4/2003 | Stivland | A61M 25/0014 156/158 |
| 7,195,611 B1 | * | 3/2007 | Simpson | A61M 25/0023 604/103.04 |
| 8,657,845 B2 | * | 2/2014 | Lentz | 606/194 |
| 8,758,295 B2 | * | 6/2014 | Schaeffer | A61F 2/958 604/102.02 |
| 2001/0029362 A1 | | 10/2001 | Sirhan et al. | |
| 2003/0105427 A1 | * | 6/2003 | Lee | A61M 25/1036 604/103.04 |
| 2005/0049552 A1 | | 3/2005 | Holzapfel et al. | |
| 2006/0264906 A1 | * | 11/2006 | Pal | A61M 25/0009 604/523 |
| 2007/0191767 A1 | * | 8/2007 | Hennessy | A61F 2/95 604/103.04 |
| 2008/0287786 A1 | * | 11/2008 | Lentz | A61F 2/95 600/435 |
| 2010/0217234 A1 | * | 8/2010 | Grovender | A61L 29/06 604/523 |

OTHER PUBLICATIONS

International Search Report for International Application No. PCT/US2010/049758, dated Feb. 15, 2011, 7 pages.

International Preliminary Report on Patentability for International Application No. PCT/US2010/049758, dated Apr. 3, 2012, 17 pages.

\* cited by examiner

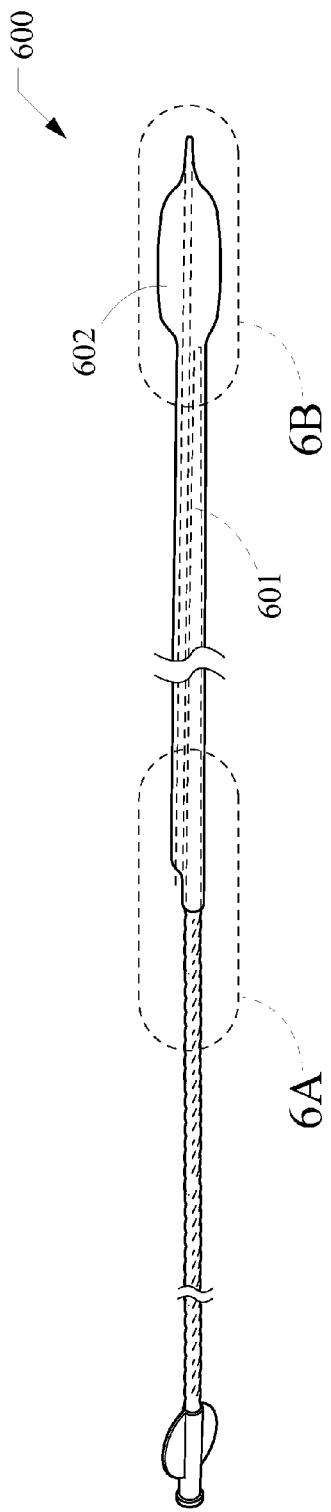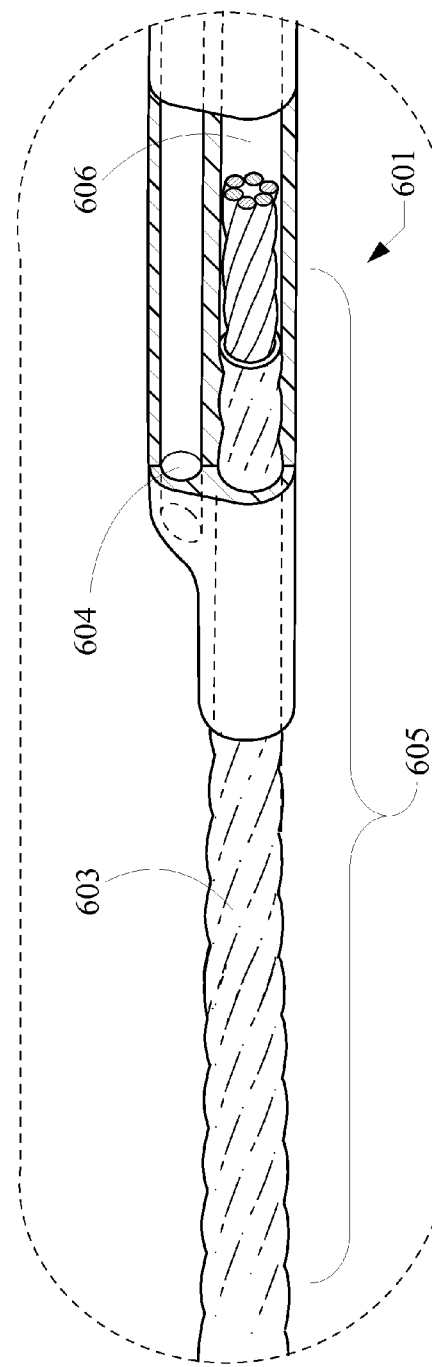
Fig. 6
Fig. 6A
Fig. 6B

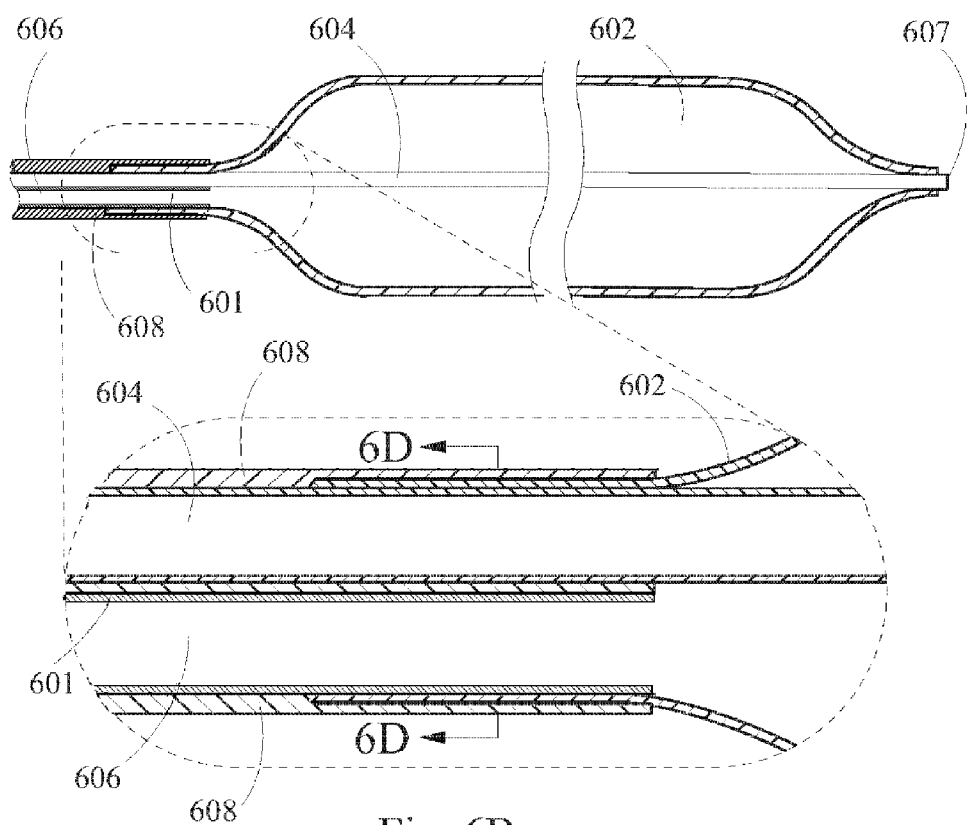
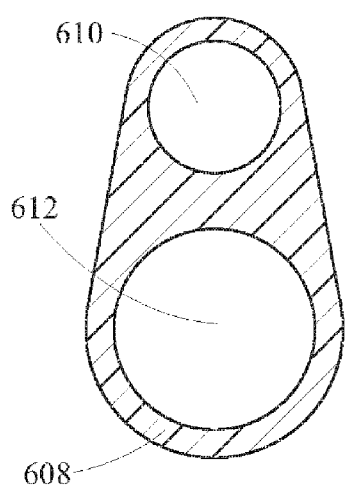
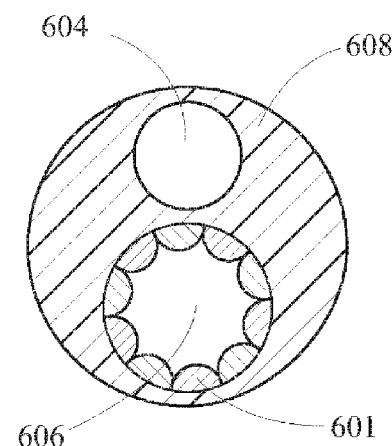
Fig. 6B
Fig. 6C
Fig. 6D

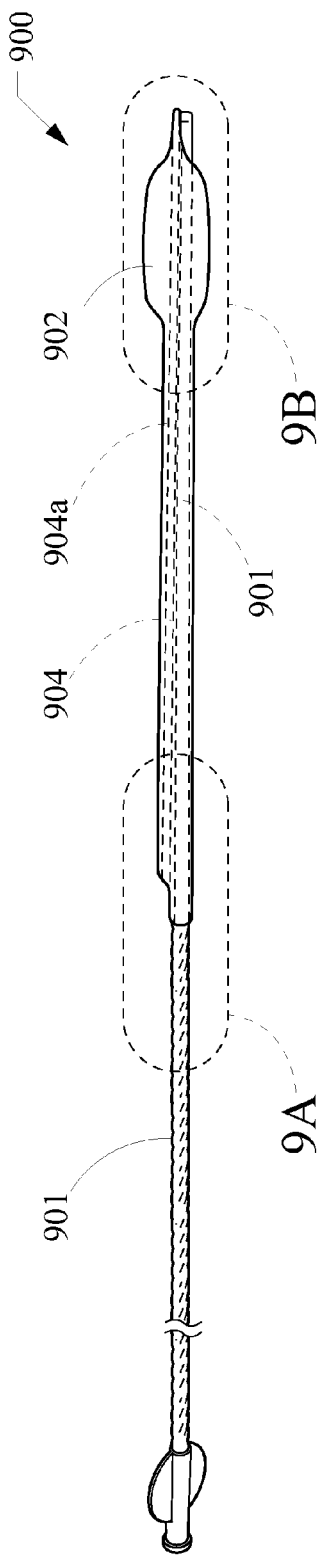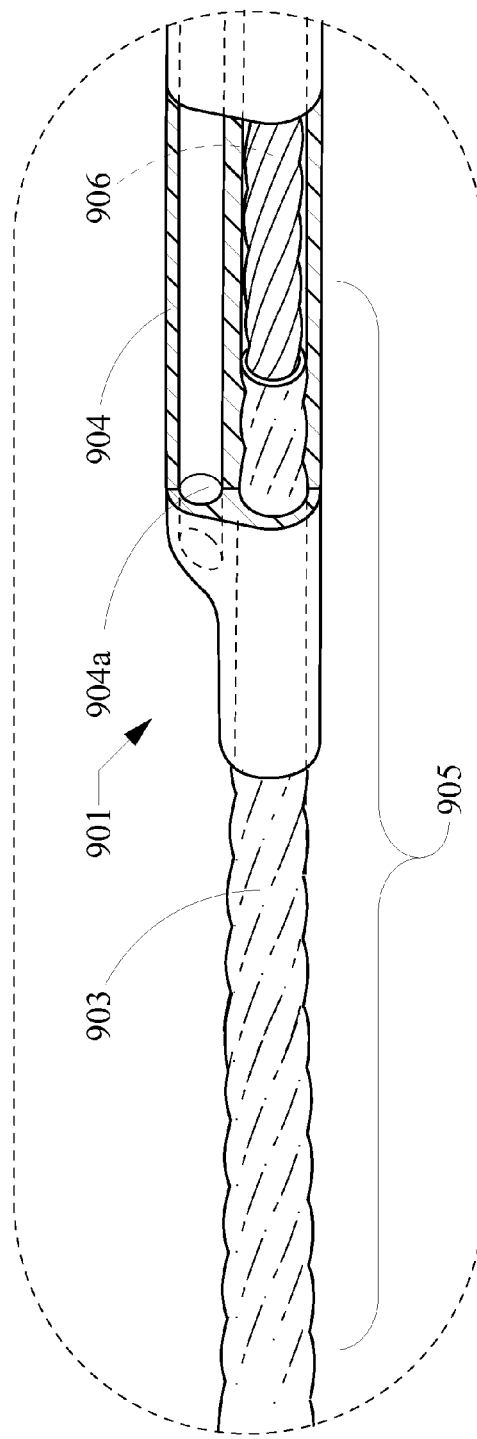
Fig. 9
Fig. 9A
Fig. 9B

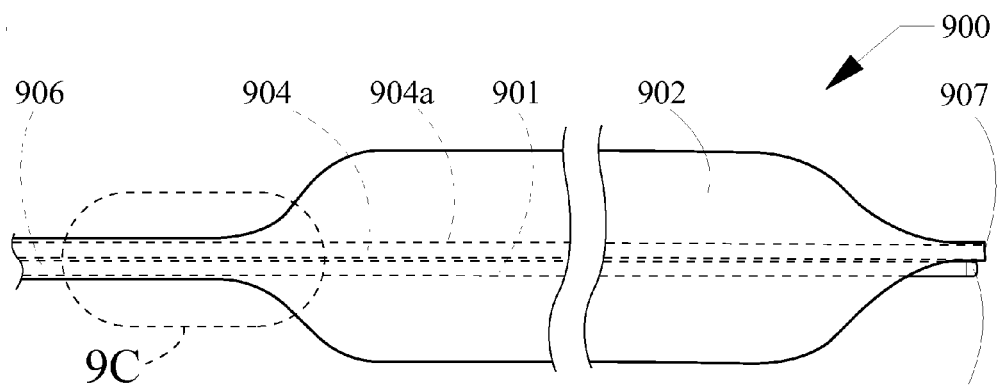
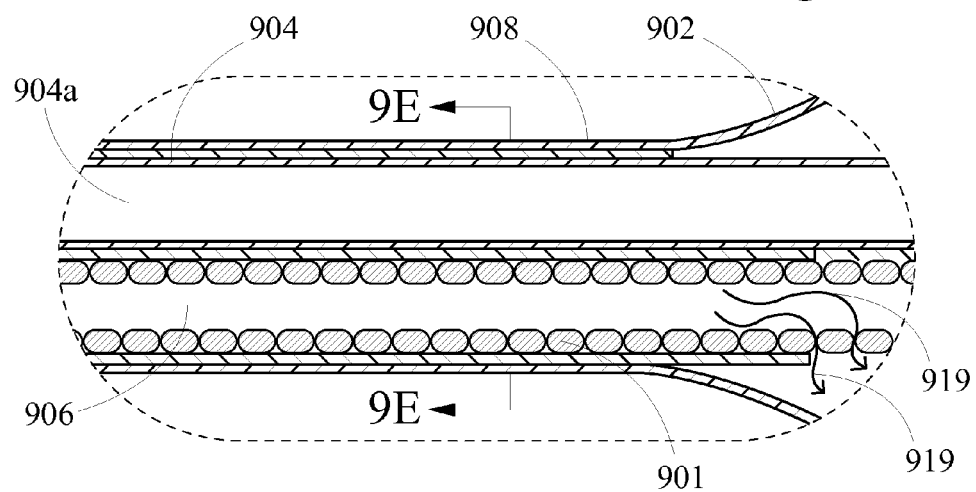
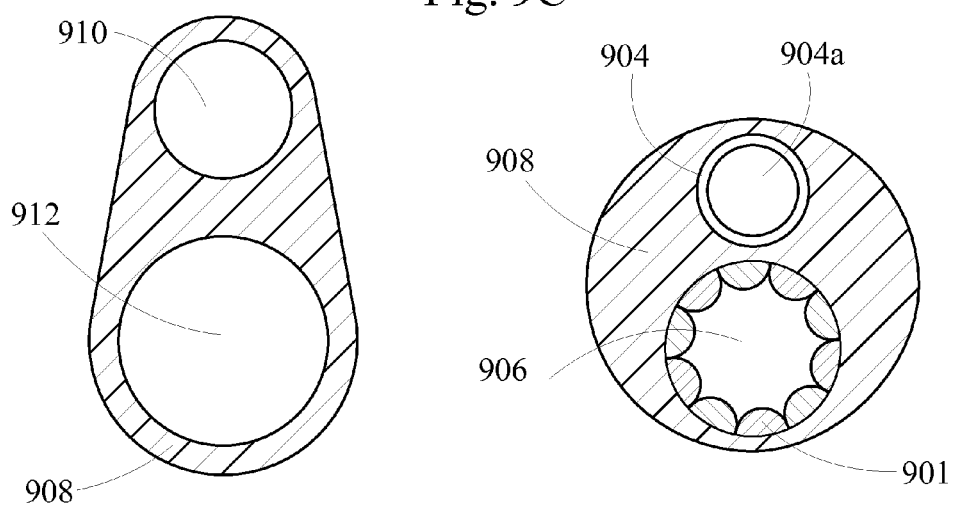

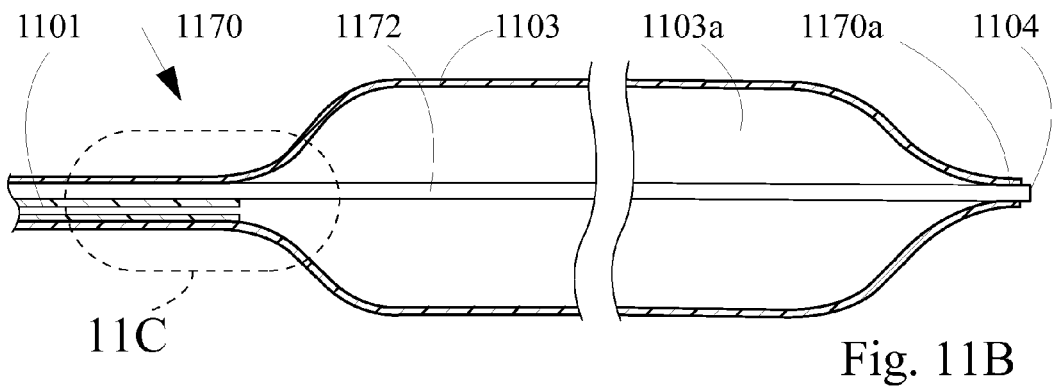
Fig. 11B
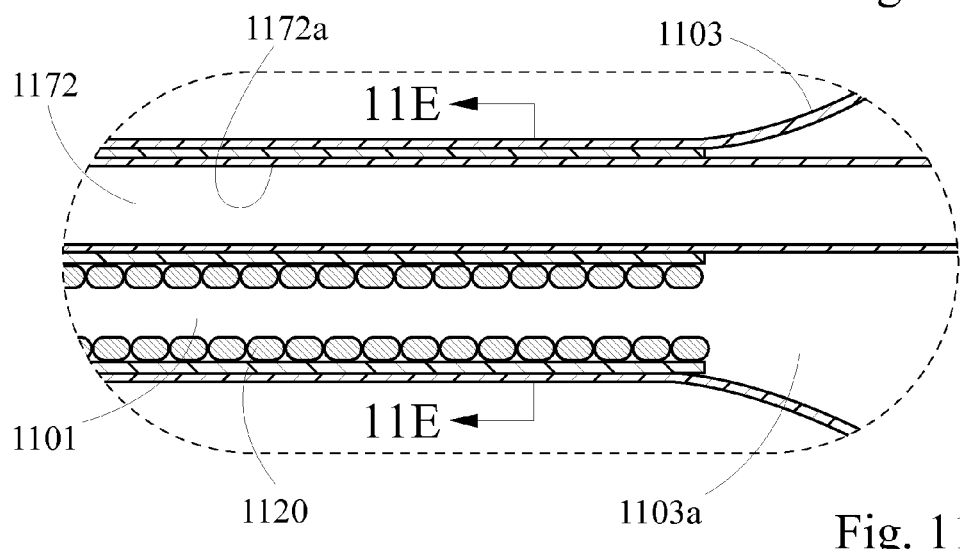
Fig. 11C
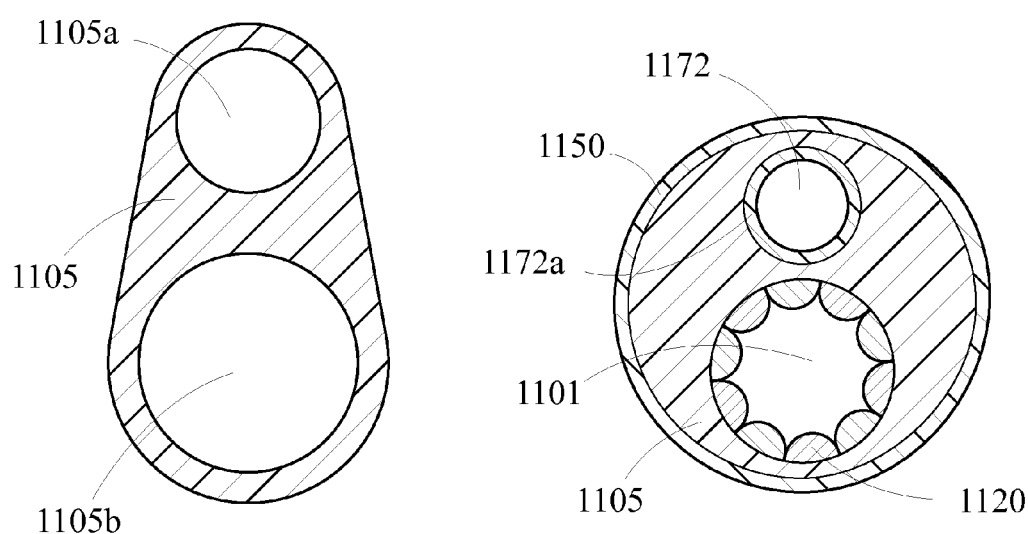
Fig. 11D
Fig. 11E

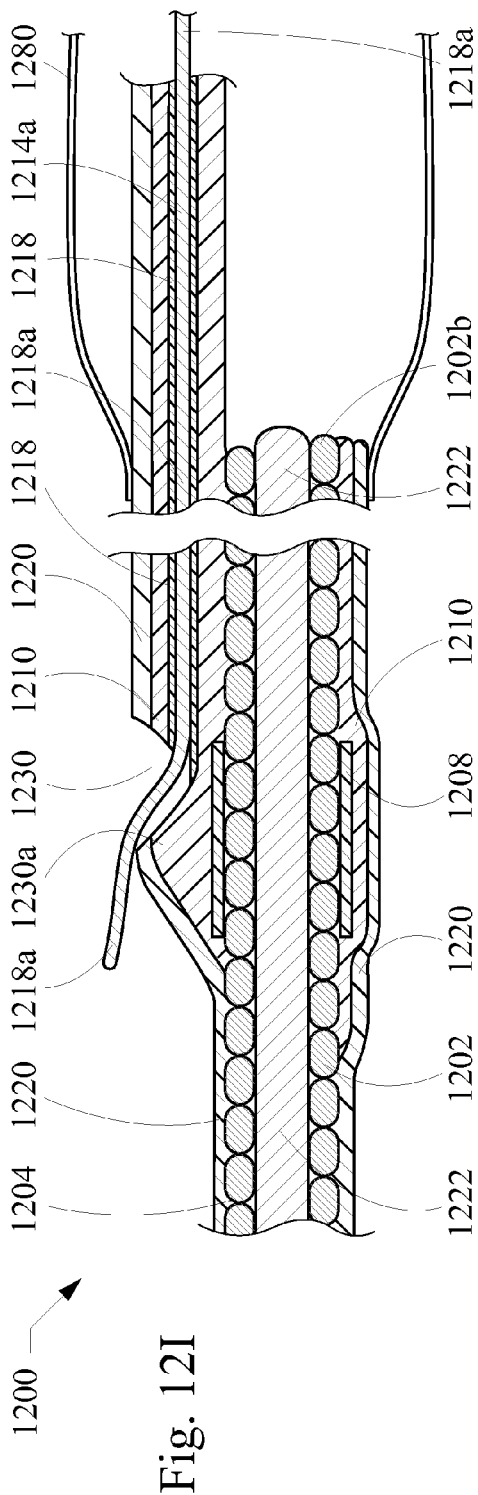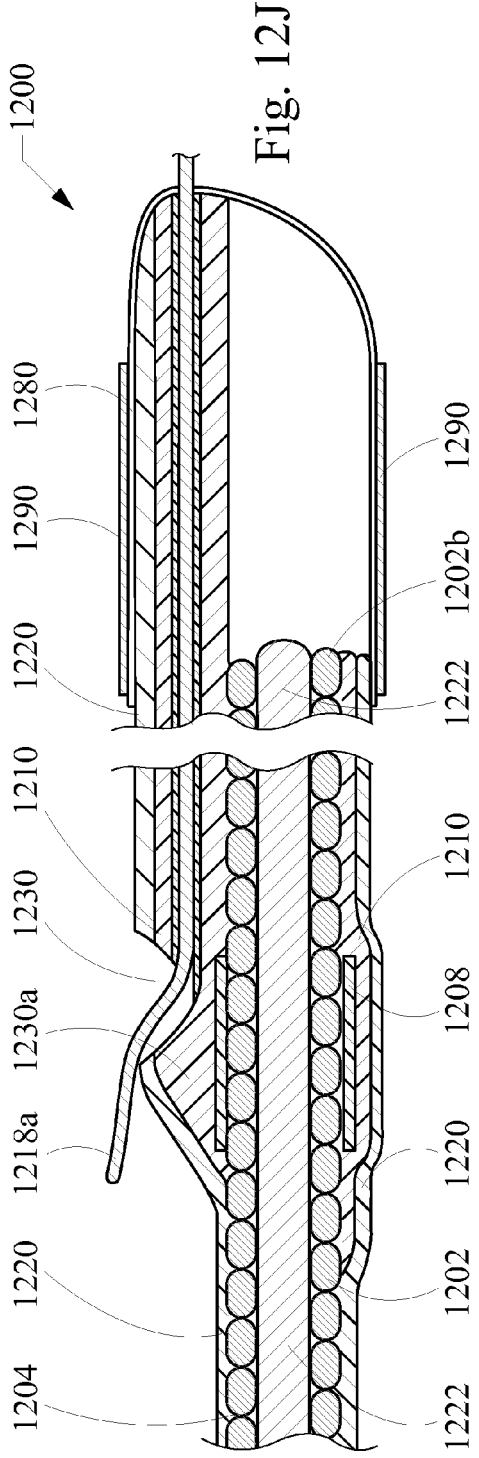

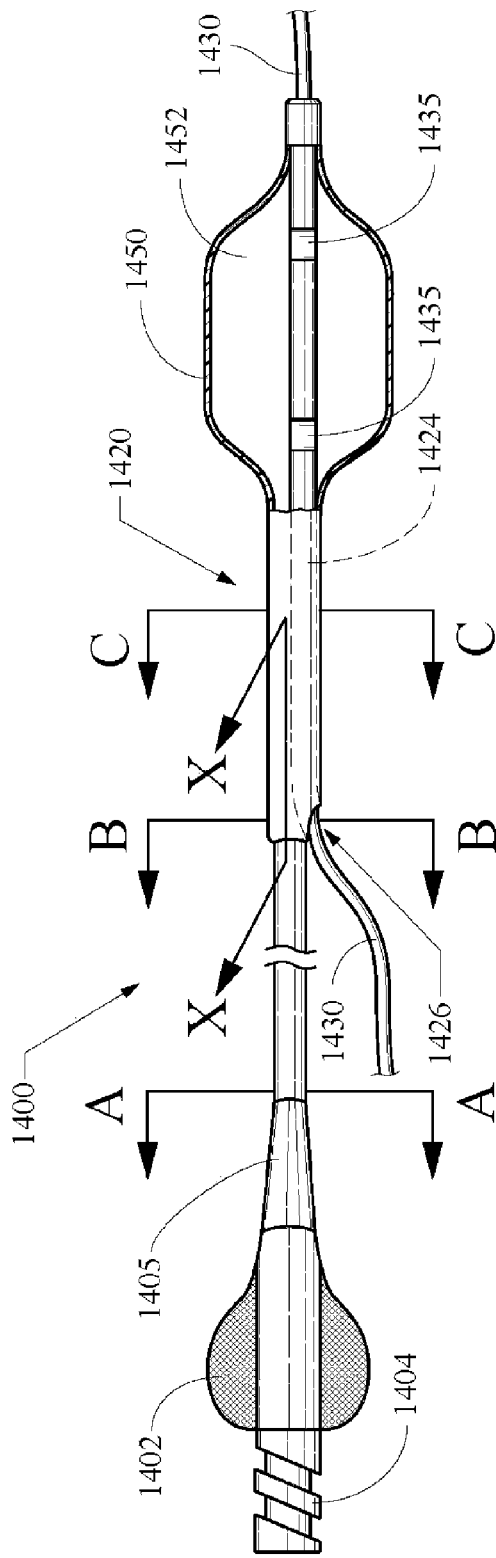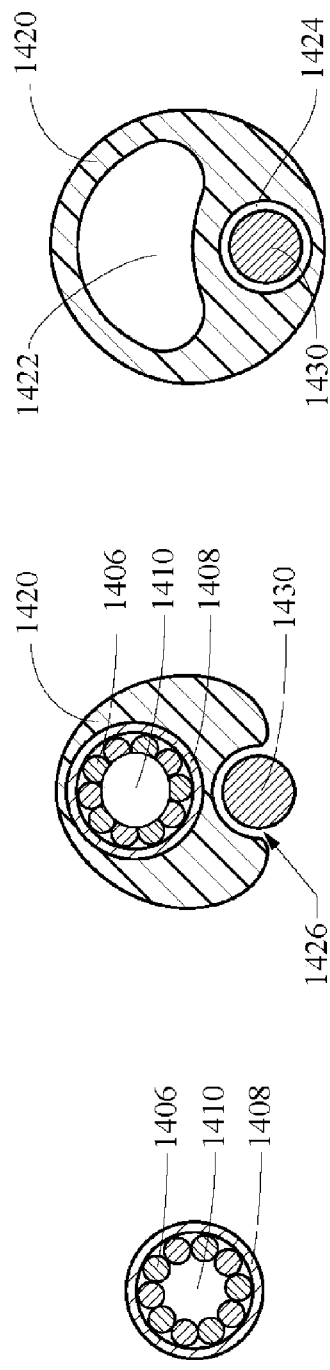
Fig. 13
Fig. 13A
Fig. 13B
Fig. 13C

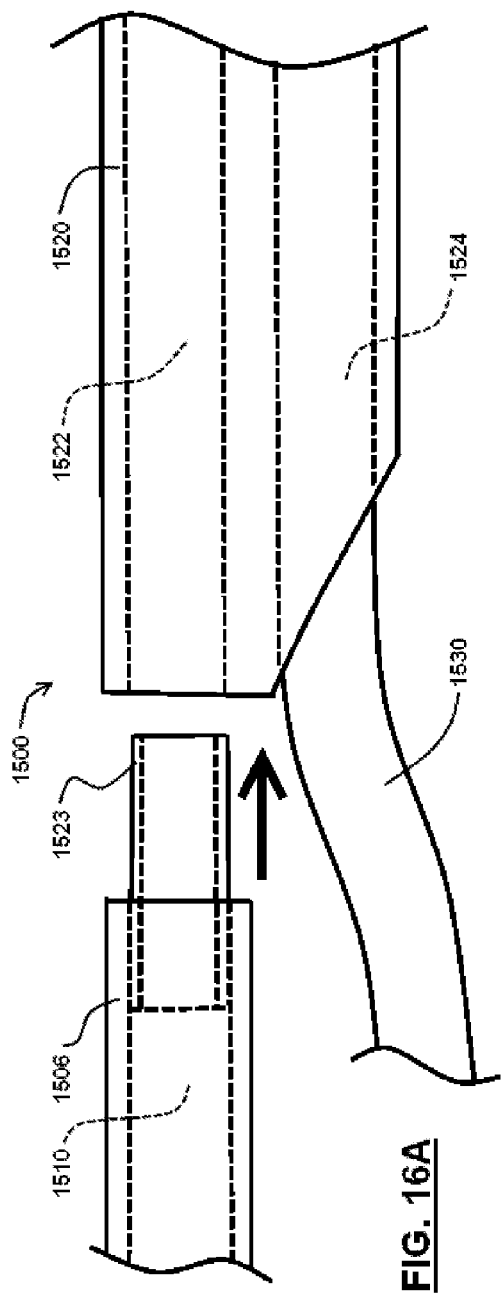
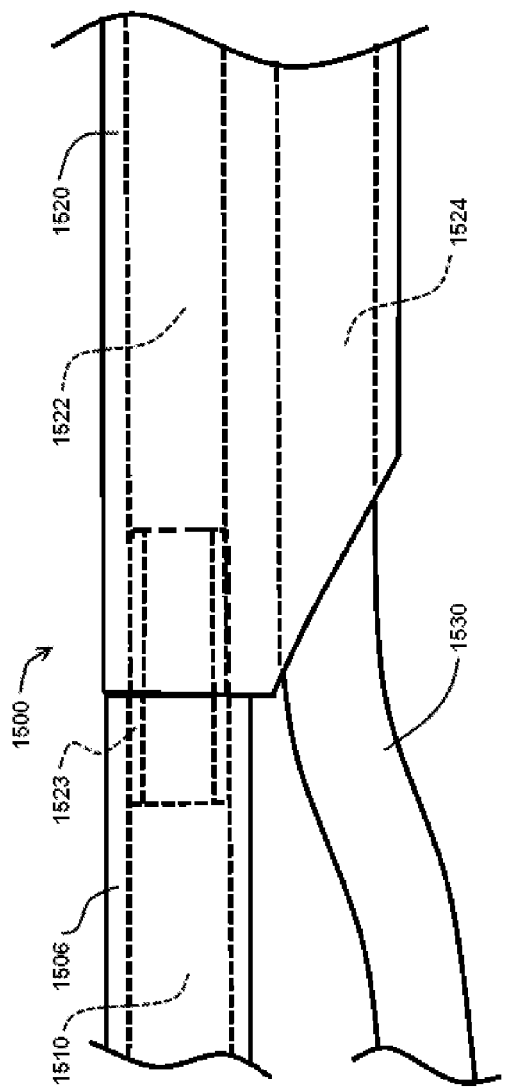

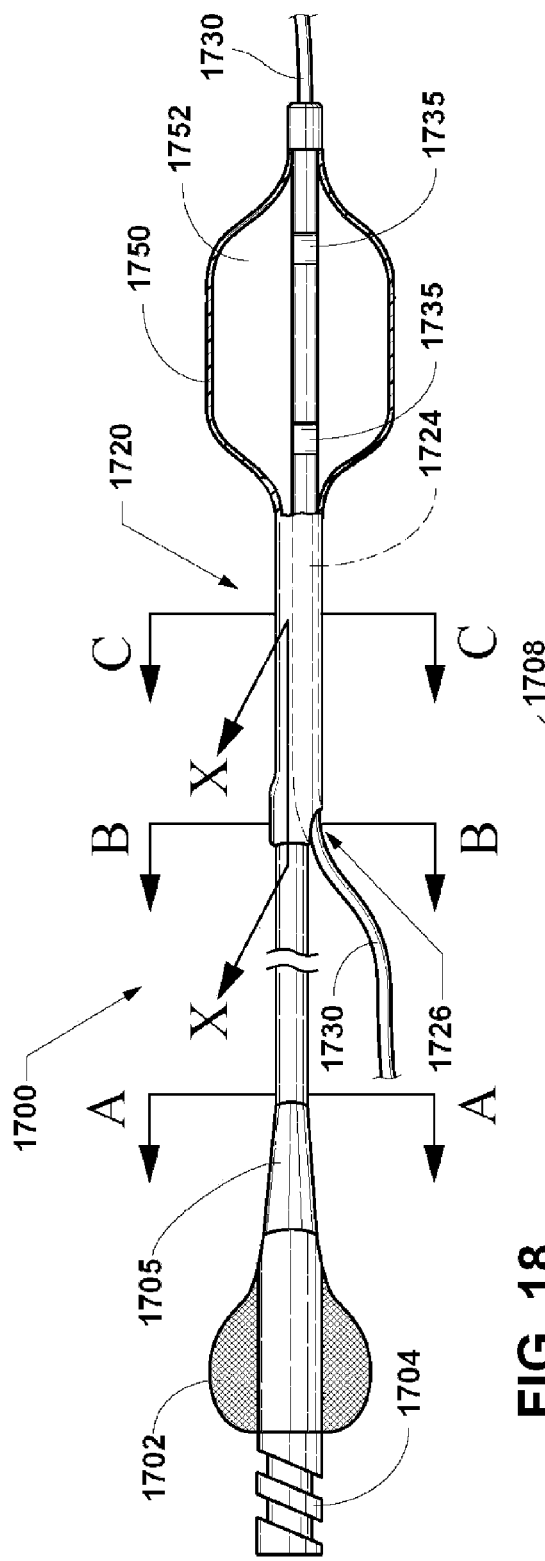
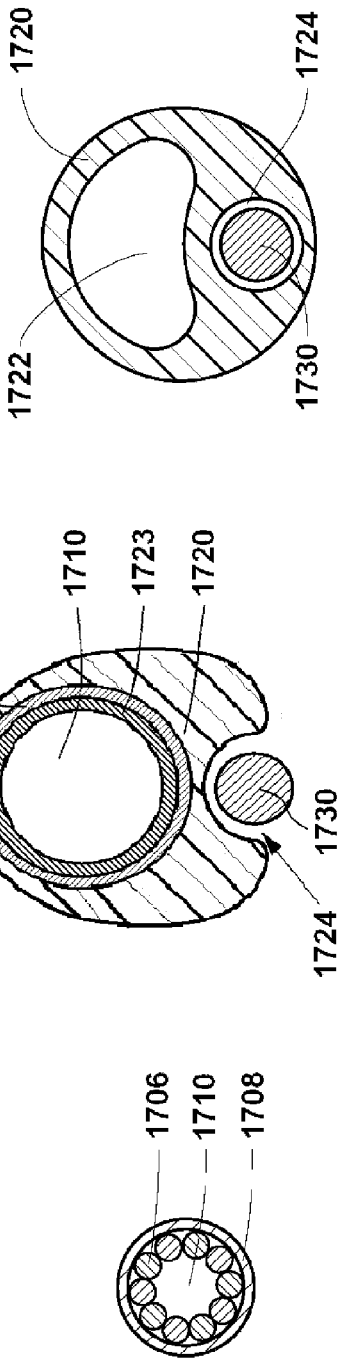
FIG. 18
FIG. 18A
FIG. 18B
FIG. 18C

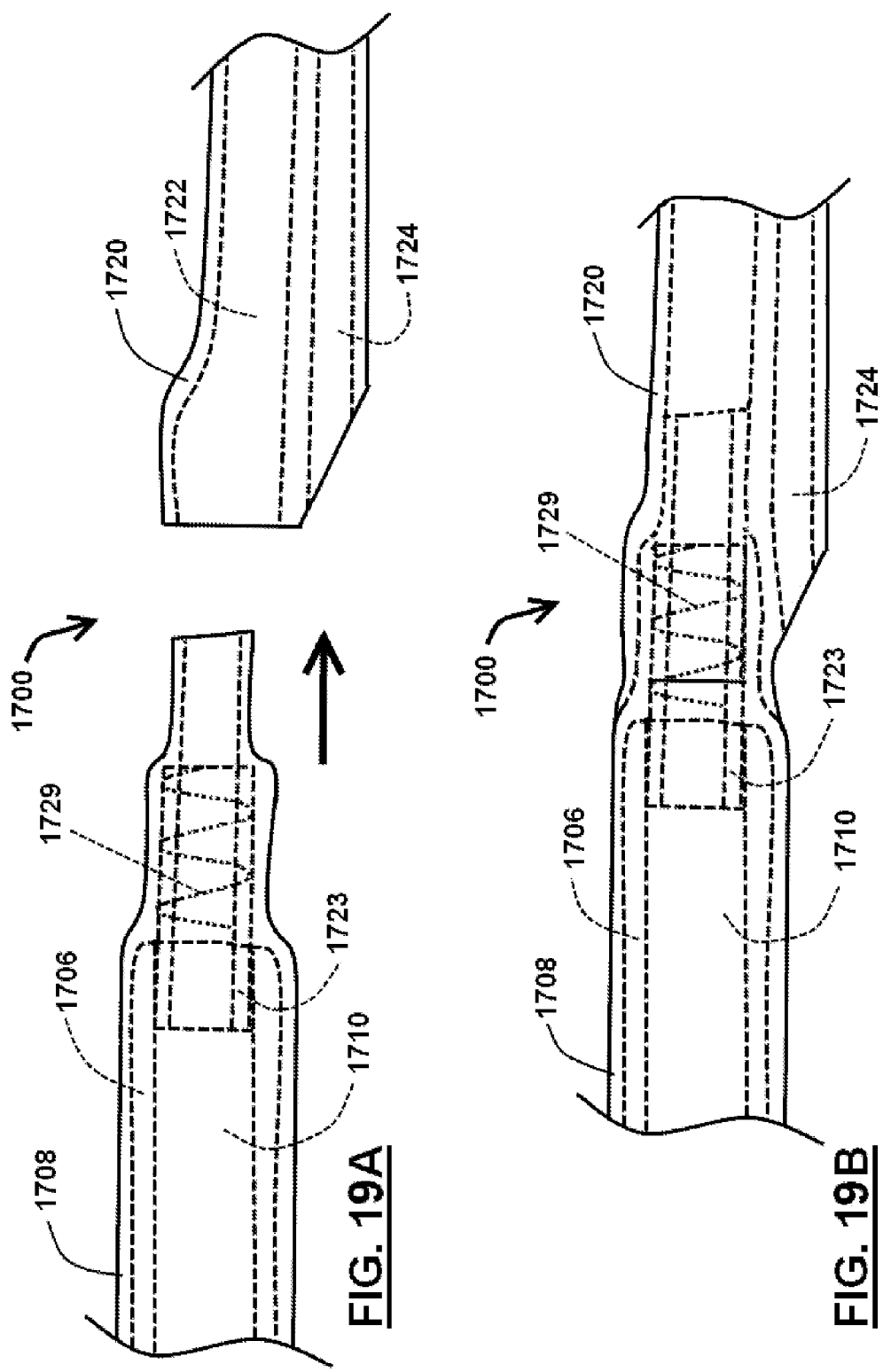

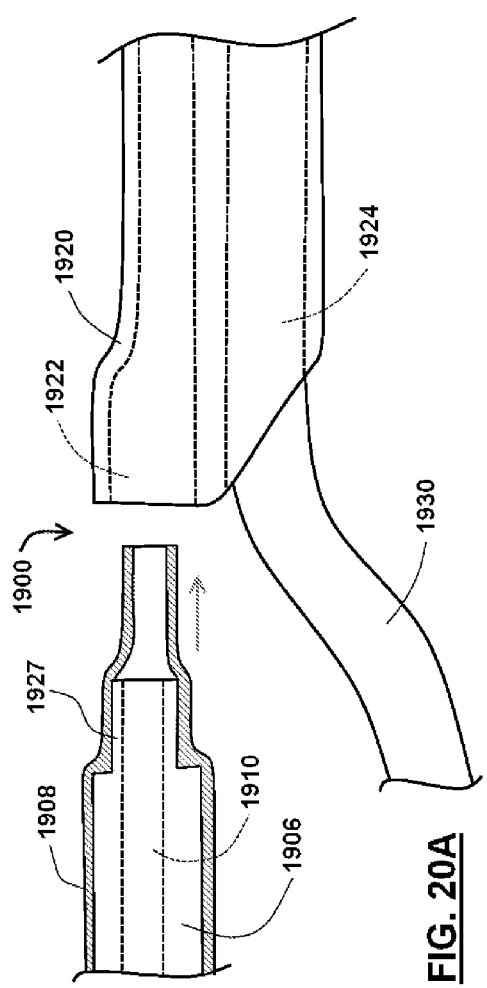
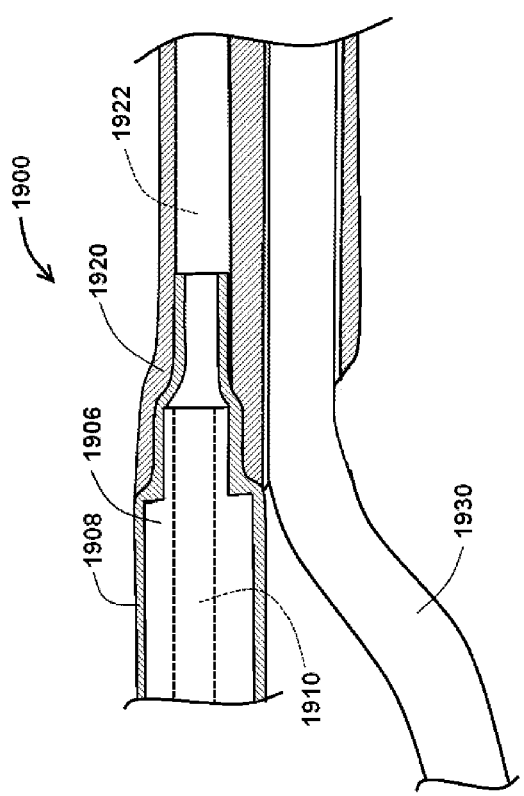
FIG. 20A
FIG. 20B

SHORT WIRE CABLE CATHETER

RELATED APPLICATIONS

The present application is a continuation of U.S. patent application Ser. No. 13/498,373, filed Mar. 27, 2012, filed under 35 USC §371 out of Application Ser. No. PCT/US10/49758, which was filed Sep. 22, 2010, out of provisional U.S. Patent Application Ser. No. 61/247,175, filed Sep. 30, 2009, and 61/367,534, filed Jul. 26, 2010, each of which is incorporated herein by reference, and from each of which the present application claims the benefit of filing date and priority.

TECHNICAL FIELD

The present application relates to medical catheters, and more specifically to medical balloon catheters useful in endovascular and other body lumens.

BACKGROUND

Medical delivery catheters are well known in the art of minimally invasive surgery for introduction of fluids and devices to sites inside a patient's body. For example, balloon dilation of luminal stenoses (e.g., in procedures such as angioplasty or balloon dilation of a bile duct), stent placement, and introduction of radio-opaque contrast fluids are common uses of catheters.

The most widely used form of angioplasty makes use of a dilation catheter having an inflatable balloon at its distal end. In coronary procedures, a hollow guide catheter or wire guide typically is used for guiding the dilation catheter through the vascular system to a position near the stenosis (e.g., to a coronary arterial lumen occluded by plaque). Using fluoroscopy, the physician guides the dilation catheter the remaining distance through the vascular system until a balloon is positioned to cross the stenosis. The balloon is then inflated by supplying pressurized fluid, through an inflation lumen in the catheter, to the balloon. Inflation of the balloon causes a widening of the lumen of the artery to reestablish acceptable blood flow through the artery. In some cases, a stent may be deployed with or instead of the balloon to widen and hold open the occluded arterial lumen.

Preferably a catheter used in endovascular lumens will have several physical characteristics. The profile and shaft size of the dilation catheter should be such that the catheter can reach and cross a very tight stenosis. Portions of the dilation catheter must also be sufficiently flexible to pass through a tight curvature or tortuous passageway, especially in a catheter adapted for use in the coronary arteries. The ability of a catheter to bend and advance effectively through the endovascular or other lumens is commonly referred to as the "trackability of the catheter." Another important feature of a dilation catheter is its "pushability." Pushability involves the transmission of longitudinal forces along the catheter from its proximal end to its distal end so that a physician can push the catheter through the vascular or other lumenal system and the stenoses. Effective catheters should be both trackable and pushable.

Two commonly used types of dilation catheters are referred to as "long-wire" catheters and "short-wire" catheters. A long-wire catheter is one in which a wire guide lumen is provided through the length of the catheter that is adapted for use with a wire guide that can first be used to establish the path to and through a stenosis to be dilated. The dilation catheter can then be advanced over the wire guide until the balloon on the catheter is positioned within the stenosis.

In short-wire catheters, the wire guide lumen may not extend the entire length of the catheter. In this type of catheter, the wire guide lumen may extend only from the distal end of the balloon to a point intermediate the distal and proximal ends of the catheter. This shorter lumen is the only portion of the catheter contacting the wire guide. It is sometimes desirable to exchange this first catheter and/or balloon for a second catheter (e.g., to "exchange out" a balloon catheter, and then "exchange in" a stent-deployment catheter). The exchange is preferably executed by leaving the wire guide in place during removal of the first catheter and using it as a guide for the second catheter. The first catheter is withdrawn or otherwise removed over the wire guide, and then a second catheter is introduced over the wire guide.

Short-wire catheters are often easier to exchange than catheters having the wire guide lumen extending the entire length of the catheter. This is because the wire guide need not be as long as a "long wire" configuration, which requires that a length of the wire guide extending outside the patient's body be longer than the portion of the catheter extending over the long wire guide in order for a doctor or assistant to maintain a grasp on the wire guide (to avoid undesired movement or displacement thereof). The short wire guide configuration catheters also create less friction during mounting and exchange operations due to the shorter wire guide lumen, leading to a reduced likelihood of displacing the wire guide.

Catheters for use in endovascular lumens typically require a variation in physical properties along different portions thereof. For example, a certain degree of stiffness is required for pushability and trackability near the proximal end while distal end requires a great deal of flexibility. A catheter having uniform properties throughout its length poses disadvantages in that it is likely to be too proximally flexible or too distally stiff. As a result, most catheter shafts (especially endovascular catheters) are made from multiple materials along the shaft length. For example, a catheter shaft may have a stiff proximal portion made of metal hypotube, a middle portion made of a stiff plastic, and a distal portion made of a more flexible plastic. This combination of materials poses problems of cost and efficiency in construction, and the junctions provide problematic possibilities for structural failure (such as binding, kinking, or even separation) as well as requiring specialized connection means. In another example, a catheter shaft may be made of plastic for a major part of its length, but have a stiffening wire disposed through a significant portion of that length to enhance stiffness. Some long wire catheters rely almost wholly on placement of a wire guide therethrough to retain the needed stiffness, which presents the problems of length and unwieldiness discussed above. In contrast, the proximal sections of short wire catheters must have adequate stiffness independent of the wire guide.

BRIEF SUMMARY

In one aspect the present invention provides a catheter device, adaptable for use in endovascular lumens or other body lumens, that has a construction of multifilar cable tubing for a substantial portion of its length and that is adaptable for use in a short-wire or long-wire configuration. The embodiments described and claimed herein provide a multifilar catheter shaft having good pushability and trackability. Embodiments of the present invention may be adaptable for a variety of applications (e.g., placement of expandable stents, balloon dilation of stenoses) and use in a variety of surgical locations (e.g., vascular, gastroenterological). The embodiments herein may be adaptable for use in a variety of minimally invasive surgical treatments (including, e.g., angioplasty or bile duct dilation).

BRIEF DESCRIPTION OF THE DRAWINGS

FIG. 6 is a side view of a tapered catheter device having an external distal wire guide lumen structure and an inflation balloon;

FIG. 6A is a detail of FIG. 6 and shows a longitudinal cross-sectional view of the tapering portion and external wire guide lumen of a catheter device;

FIG. 6B is a detail of FIG. 6 and shows a longitudinal cross-sectional view of the distal portion of the catheter device, with an enlarged detail view of features where the catheter shaft meets the balloon;

FIG. 6C is a transverse cross-sectional view of a dual-lumen mounting sleeve;

FIG. 6D is a transverse cross-sectional view along line 6D-6D of FIG. 6B showing two lumens of the catheter device surrounded by a mounting sleeve;

FIGS. 9-9E depict still another catheter device embodiment, including a wire guide lumen tube.

FIGS. 11A-11B are detail views of FIG. 11;

FIG. 11C is a longitudinal cross-sectional view of a dual-lumen mounting sleeve;

FIGS. 11D-11G show transverse cross-sectional views of the catheter device of FIG. 11;

FIGS. 12A-12K show one method of making a catheter of the present invention;

FIGS. 13 and 13A-13C show another catheter embodiment and three section views of that embodiment, along lines A-A, B-B, and C-C, respectively;

FIGS. 16A and 16B show, respectively, partially unassembled and assembled proximal and distal catheter portions of a catheter embodiment;

FIG. 18 shows a partial-section longitudinal side view of the assembled catheter embodiment of FIGS. 17A-17B;

FIGS. 18A-C show transverse section views of the catheter embodiment of FIG. 18;

FIGS. 19A and 19B show, respectively, partially unassembled and assembled proximal and distal catheter portions of a catheter embodiment that includes an alternative feature for the catheter embodiment of FIGS. 17A-17B; and FIGS. 20A and 20B show, respectively, partially unassembled and assembled proximal and distal catheter portions of another catheter embodiment.

DETAILED DESCRIPTION

Figure 1:
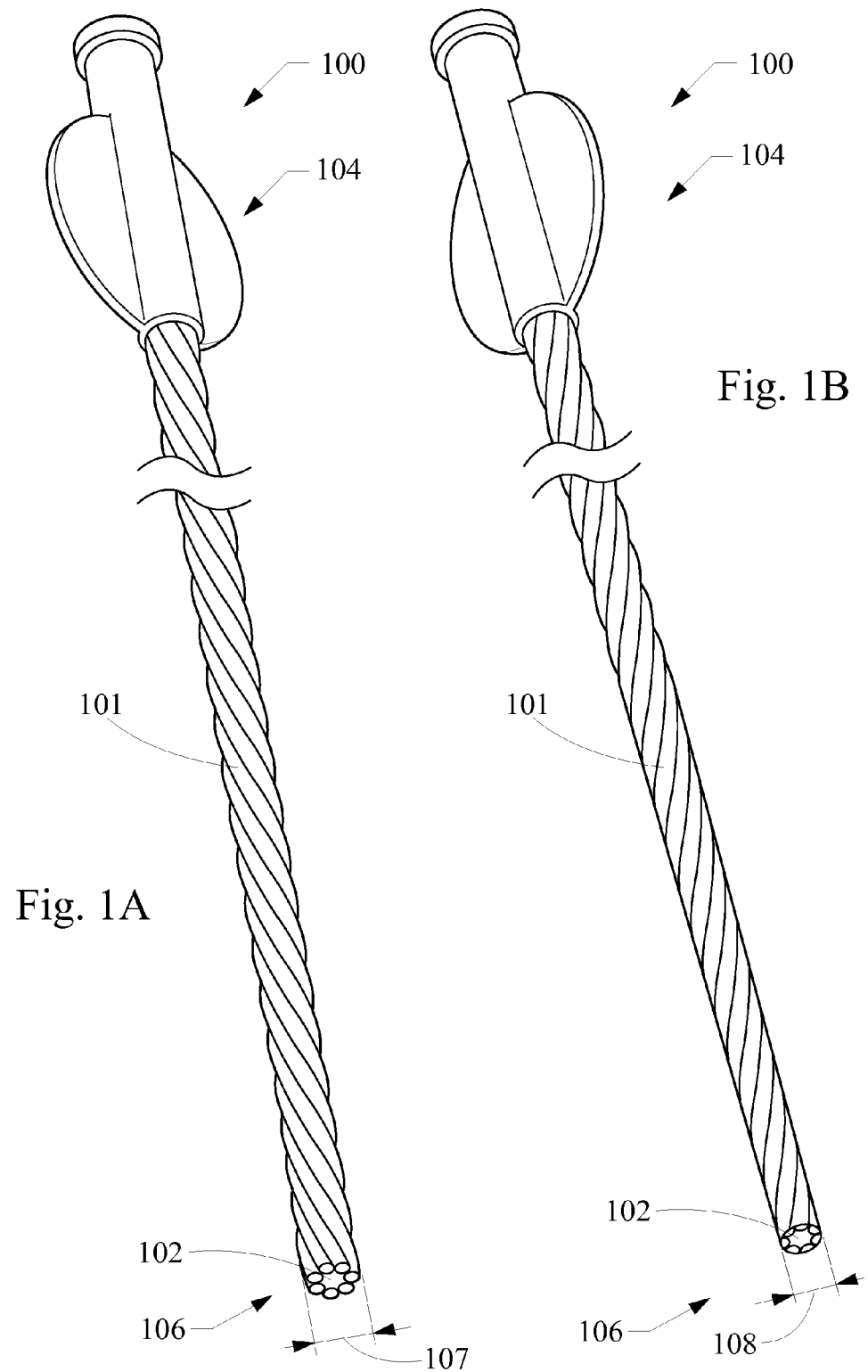
FIG. 1A is a perspective view of a catheter, with an enlarged detail view of the catheter's distal end.
FIG. 1B is a perspective view of a tapered catheter device, with an enlarged detail view of the catheter's distal end.

In one aspect, presently described embodiments of a multifilar tube catheter shaft may be adaptable for use in a variety of minimally invasive surgical applications (e.g. endoscopic procedures, central or peripheral cardiovascular intervention procedures such as, for example, angioplasty).

The embodiments are described with reference to the drawings in which like elements are generally referred to by like numerals. The relationship and functioning of the various elements of the embodiments may be understood by reference to the drawings and the following detailed description. However, the embodiments described are provided by way of example only, and the invention is not limited to the embodiments illustrated in the drawings. It should also be understood that the drawings are not necessarily to scale, and—in certain instances—details have been omitted that are not necessary for an understanding of the embodiments such as conventional details of fabrication and assembly. Specifically, with reference to scale, the proportion of wall thickness to lumen size and other components shown is not drawn to scale in many of the embodiments illustrated herein. Throughout the specification, the terms "distal" and "distally" shall denote a position, direction, or orientation that is generally away from the physician (including any other person holding/operating a device) and/or toward a treatment zone/patient. Accordingly, the terms "proximal" and "proximally" shall denote a position, direction, or orientation that is generally towards the physician.

FIGS. 1A-1B illustrate an embodiment of a catheter device 100 with a shaft 101 constructed of a multifilar material (also known as cable tubing) and having an internal lumen 102. The multifilar tubing described is made of a plurality of wires twisted together and leaving a central lumen. Such multifilar tubing may be obtained, for example, from Asahi-Intecc (Newport Beach, Calif.) or from Fort Wayne Metals (Ft. Wayne, Ind.) as Helical Hollow Strand®. Materials and methods of manufacturing suitable multifilar tubing are described in Published U.S. Pat. No. 7,117,703 (Kato et al.), the contents of which are incorporated herein by reference. Use of multifilar tubing in a vascular catheter device is described in U.S. Pat. No. 6,589,227 (Sonderskov Klint, et al.; Assigned to Cook Inc. of Bloomington, Ind. and William Cook Europe of Bjaeverskov, Denmark), which is also incorporated herein by reference. As illustrated in the embodiments shown herein, a preferred multifilar tubing of the present invention may include a monolayer or multilayer multifilament tubing, which includes at least one columnar layer of generally parallel filars and is distinguished from cross-wound multifilar tubing or braided tubing where fibers are interlaced, interwoven or otherwise overlapped as is known and used in the art. Described another way, a preferred multifilar tubing of the present invention includes a wire-stranded hollow coil body, which includes a plurality of coil line elements stranded along a predetermined circular line to form a flexible linear tube having a central axial hollow portion forming a lumen. In addition, preferred multifilar tubing of the present invention is distinguished from multifilar wire guides as having a fluid-patent lumen configured for efficient fluid communication (e.g., of pressurized inflation fluid; the terms "patent," "fluid-patent," and derivatives thereof are used herein to describe a lumen or other passage through which a fluid may travel with essentially no leakage). A preferred monolayer multifilar tubing provides desirable pushability and trackability with low probability of kinking. The monolayer tubing may include interior or exterior coatings. However, it should be noted that spiral-cut and non-spiral-cut hypotube may also be used within the scope of the invention in the following embodiments wherever multifilar/cable tube is described (unless hypotube is specifically excluded). Generically, the term "metal alloy tube" may be used to describe multifilar and/or hypotube, but the use of any of these terms herein should generally be understood to include or be interchangeable with the others, unless specifically excluded.

In FIG. 1A, the exterior diameter 107 is approximately the same along the length of the shaft 101. In the embodiment shown in FIG. 1B, the proximal end 104 has a greater exterior diameter than the distal end 106. The catheter shaft 101 tapers toward a smaller exterior diameter 108 at the distal end 106. Tapering can enhance flexibility of the shaft 101 in several ways. For example, flexibility is enhanced by decreasing the outside diameter of the catheter shaft 101. The portion of the catheter shaft 101 having a smaller diameter is more flexible than the portion having a larger diameter. Such tapering also decreases the thickness of the wall of the catheter shaft 101. Alternatively, tapering may be used within the internal diameter of a catheter, enhancing flexibility by decreasing wall thickness without altering the exterior diameter of the shaft 101. The steepness and location of the tapering is determined by the desired application for the catheter shaft 101. For example, in alternative embodiments, there may be multiple stepwise or gradual differences in diameter to confer different degrees of flexibility throughout the length of the catheter. For example, catheter shaft 101 for use in coronary arteries will typically benefit from a smaller diameter than a catheter shaft 101 for use in a bile duct, both for gross size and flexibility. A grinding process or other suitable process may be used to reduce the exterior diameter as appropriate for the desired application. Reducing the exterior diameter provides an added benefit by reducing the profile of the device. The flexibility of the catheter shaft 101 or a portion thereof may also be altered by increasing or decreasing the number of filars. In one aspect, the embodiments described herein also provide a catheter shaft having consistent construction material throughout most of the length of the catheter shaft, with gradual transition from a stiffer proximal end to a more flexible distal end and lacking sharp transitions that undermine structural integrity.

A further embodiment of the catheter shaft 101 includes a coating on internal and/or external surfaces for at least a portion of the catheter shaft 101. The coating is selected to confer or improve one or more properties of reduced friction, flexibility, and sealing a lumen 102 of the catheter. Sealing the lumen 102 allows the lumen to be used, for example, for introduction of inflation fluid to a dilation balloon or introduction of a medicative substance or radio-opaque contrast fluid.

Figure 2:
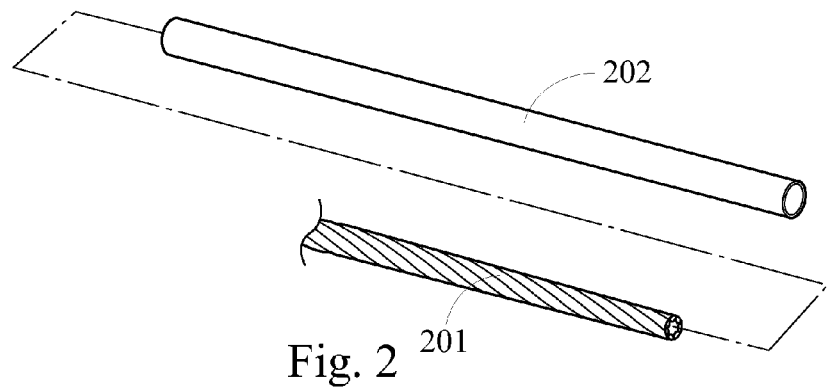
FIG. 2 is a perspective view of a catheter shaft with a sleeve.

The coating may be, for example, a sheath or sleeve 202 as illustrated in FIG. 2. In various alternative embodiments, the sheath 202 may comprise an extruded sleeve, shrink tube, extruded over-jacket, or dip coat. The sheath 202 is preferably a thermoset material or a thermoplastic material and may comprise, for example, HDPE, PTFE, PET, polyester or polyether block amide (PEBA), polyurethane, polyimide, polyolefin, nylon, or any combination thereof. The coating may be applied by, for example, over-extrusion, dip-coating, melt fusion, or heat shrinking. For example, PET shrink tube 202 has the advantage of providing an increased stiffness to a small diameter catheter shaft 201. On the other hand, a PEBA shrink tube 202 can be used with a larger diameter catheter shaft 201 where greater flexibility is desired. The type of sleeve 202 material may also be selected to complement other catheter components; for example, a nylon sleeve 202 may bond and interact better with a nylon expandable member (e.g., balloon or basket) and/or a nylon wire guide lumen. Selection of coating materials, filar size and number, and diameter allow manipulation of the catheter shaft's shore hardness to offer the desired functional properties.

Figure 3A:
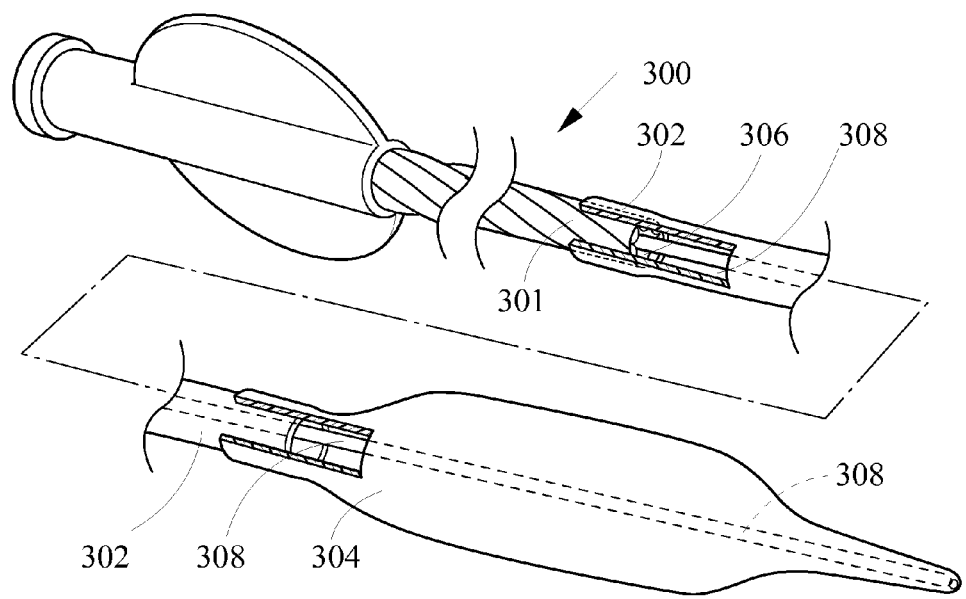
FIG. 3A is a perspective view of a catheter device having a distal extension and an inflation balloon, with an enlarged detail view of the features at the catheter's distal end.
Figure 3B:
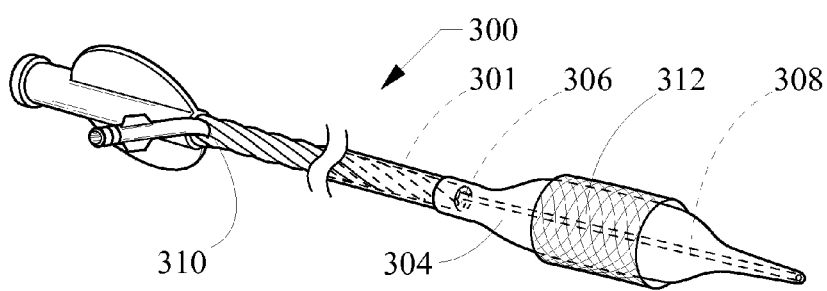
FIG. 3B is a perspective view of a catheter device with an inflation balloon.

FIGS. 3A-3B illustrate embodiments of balloon catheters 300 comprising a multifilar shaft 301. In the embodiment of FIG. 3A, the catheter shaft 301 has a distal extension 302, upon which is mounted an inflation balloon 304. The distal extension 302 can be formed of the same group of materials used in the coating (HDPE, PTFE, PEBA, PET, polyurethane, polyimide, polyolefin, nylon, or any combination thereof) and provides a shaft portion that may be more flexible than the shaft 301. As can clearly be seen in the detail illustration portion of FIG. 3A, the extension 302 encloses an inflation lumen 306 which continues from an inflation lumen 306 of the multifilar catheter shaft 301. The extension 302 also encloses a wire guide lumen 308. In the illustrated long wire configuration catheter 300, the wire guide lumen extends from the proximal end of the multifilar catheter shaft 301 and extends through the inflation balloon 304 at the distal end.

The embodiment illustrated in FIG. 3B has an inflation balloon 304 disposed directly on the distal end of the catheter shaft 301. An inflation lumen 306 of the multifilar catheter shaft 301 opens into the inflation balloon 304. A wire guide lumen 308 traverses the interior of the balloon 304, continuing the wire guide lumen 308 of the catheter shaft 301 to a point distal of the inflation balloon 304. As illustrated an expandable stent 312 may be positioned about the balloon 304. In an alternative embodiment, an expandable member other than a balloon (e.g., a basket) may be disposed near the distal end of the catheter shaft 301. Such an embodiment optionally may have a wire guide through the expandable member. At its proximal end the catheter 300 has a port 310 in fluid communication with the inflation lumen 306. In an alternative embodiment, the port 310 offers access to the guide wire lumen 308. The port 310 may be included in other embodiments, and in other positions on the catheter 300. In another alternative embodiment, the catheter shaft 301 has two ports 310, offering separate access to each of the inflation lumen 306 and the wire guide lumen 308. In other alternative embodiments, the port 310 may be useful for introducing another fluid such as a contrast fluid.

Figure 4A:
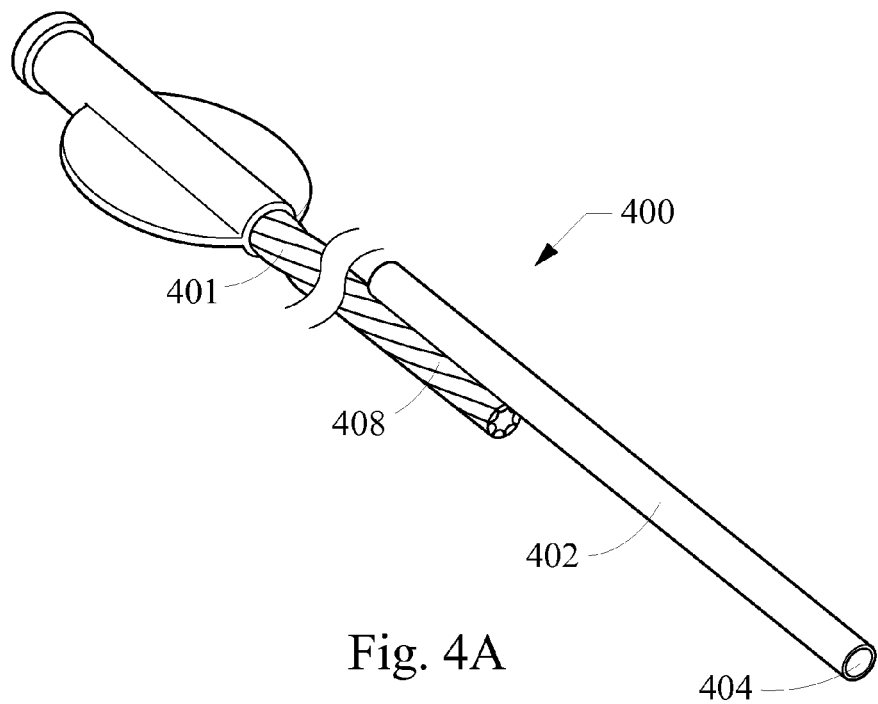
FIG. 4A is a perspective view of a catheter device having an external distal wire guide lumen structure, with an enlarged detail view of the features at the catheter's distal end.
Figure 4B:
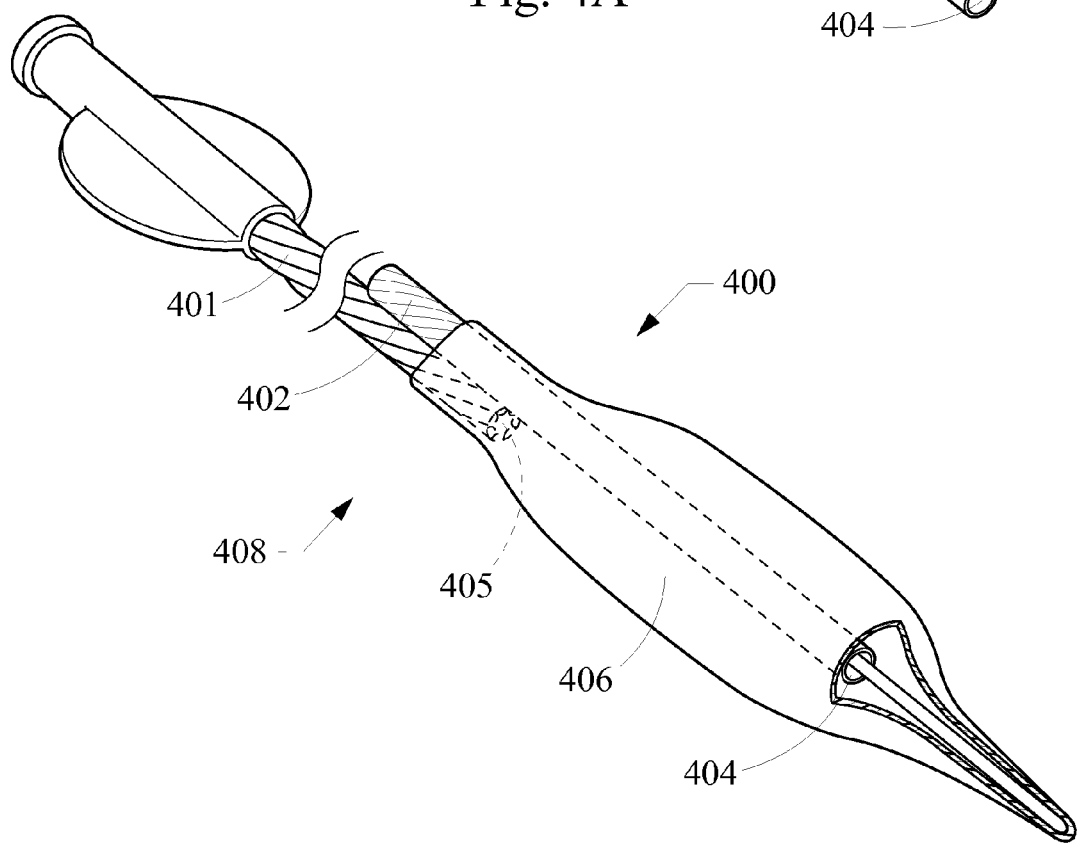
FIG. 4B is a perspective view of a catheter device having an external distal wire guide lumen structure and an inflation balloon, with an enlarged detail view of the features at the catheter's distal end.

FIGS. 4A-4B illustrate embodiments of a multifilar tube balloon catheter device 400 comprising a multifilar shaft 401 and further comprising an external, distally disposed short wire guide lumen structure in the form of a cannula 402 having a wire guide lumen 404 disposed therethrough. In FIG. 4A, the cannula 402 is attached on the distal end 408 of the multifilar catheter shaft 401 using an adhesive. Alternative means of attachment include, for example, forced convection heating, radio frequency heating, ultrasonic welding, and laser bonding. Alternatively, shrink tubing may be used as a manufacturing aid to help compress and fuse the cannula 402 to the multifilar catheter shaft 401. The shrink tubing may be removed and disposed of after the cannula 402 is connected to the catheter shaft 401, or may remain on as part of the connected structure. If the multifilar catheter shaft 401 has a coating, the cannula 402 may be bonded to the coating or directly to the catheter shaft 401. A heat shrink tubing, for example PEBA, may be applied over the entire assembly, which increases the strength of the assembly. In the embodiment shown in FIG. 4B, the cannula 402 is constructed of multifilar tubing. An inflation balloon 406 is mounted on the distal end 408 of the catheter shaft 401. An inflation lumen 405 of the catheter shaft 401 is open to the interior of the inflation balloon 406. The cannula 402 extends through the inflation balloon 406 and has an extension 407 on its distal end. A wire guide lumen 404 runs through the length of the cannula 402 and its extension 407. Although not shown, it should be appreciated that an expandable stent can be disposed about the balloon 406. The cannula 402 providing a wire guide lumen structure can be formed of HDPE, PTFE, PEBA, PET, polyurethane, polyimide, polyolefin, nylon, or any combination thereof. In one embodiment, the cannula 402 comprises a PTFE inner liner and a PEBA outer cover. Other materials may be used as an inner liner such as, for example, HDPE, PET, and polyimide.

Figure 4C:
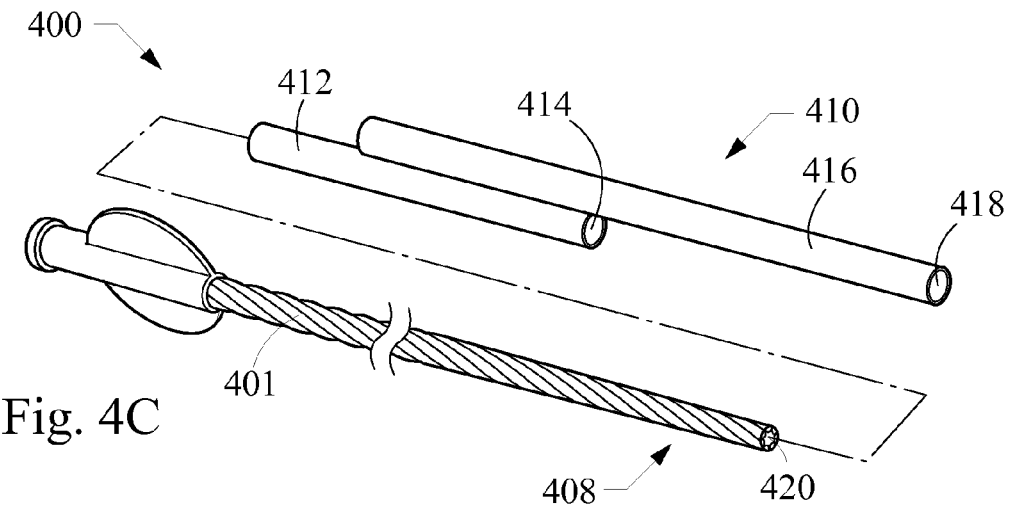
FIG. 4C is a perspective view of a catheter device with a distal dual lumen structure having a wire guide lumen structure and a mounting portion.

In FIG. 4C, a dual lumen structure 410 is disposed on the distal end 408 of the multifilar catheter shaft 401. A portion of the length of dual lumen structure 410 has a "FIG. 8" cross section. A mounting portion 412 of the dual lumen structure 410 has a lumen 414. The distal end 408 of the catheter shaft 401 fits into the lumen 414. The lumen 414 may be completely occupied by the distal end 408 of the catheter shaft 401, or may continue coaxially beyond the distal end 408 so as to form an extension. If the mounting portion 412 is placed as an extension, the lumen 414 is in fluid communication with a lumen 420 of the shaft 401. A wire guide portion 416 of the dual lumen structure 410 has a wire guide lumen 418 running therethrough. The dual lumen structure 410 is attached on the distal end 408 of the catheter shaft 401 using one of the attachment methods described for the embodiment shown in FIG. 4A. In this embodiment, the lumen 414 of the dual lumen structure is in fluid communication with a lumen 405 of the catheter shaft 401. In an alternative embodiment, a part of the mounting portion 412 is mounted inside the lumen 420 of the catheter shaft 401.

Figure 5A:
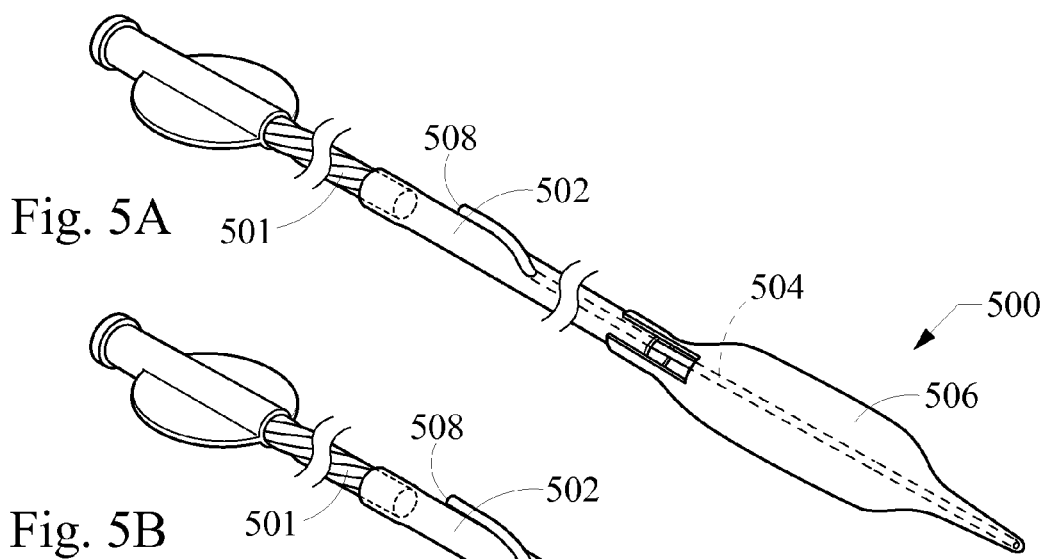
FIGS. 5A-5B show a side view of catheter devices having a distal extension and a wire guide lumen structure.
Figure 5B:
Figure 5C:
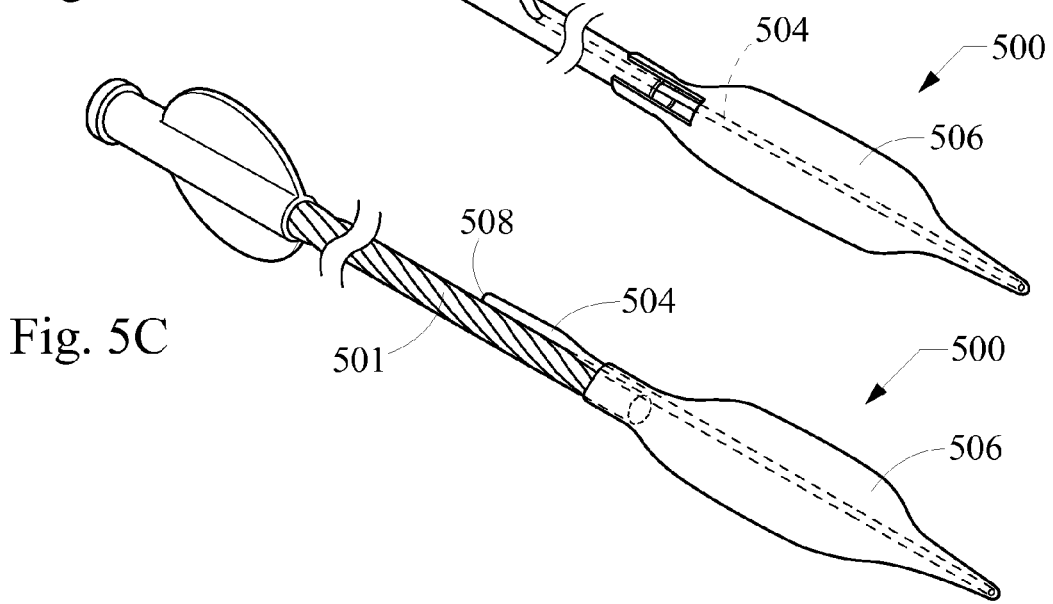
FIG. 5C is a side view of a catheter device having an external distal wire guide lumen structure and an inflation balloon.

FIGS. 5A-5C illustrate embodiments of a balloon catheter 500 incorporating a multifilar shaft 501 and having a short wire guide configuration. The embodiments shown in FIGS. 5A-5B each have a coaxial extension 502 of the multifilar shaft 501, a short wire guide lumen structure in the form of a tube 504, and an inflation balloon 506. The coaxial extension 502 may have the same or a different flexibility than the multifilar shaft 501. In the embodiment illustrated in FIG. 5A, the proximal end 508 of the tube 504 is disposed distal of the juncture of the extension 502 with the multifilar shaft 501. The tube 504 enters the extension 502 and extends through the distal end of the balloon 506. Thus, this embodiment comprises a distal extension of the shaft (in this case the coaxial extension 502) and the wire guide lumen structure 504, a portion of the wire guide lumen structure 504 being coaxial within the distal extension, another portion of the wire guide lumen structure 504 being outside the distal extension adjacent thereto.

In the embodiment illustrated in FIG. 5B, the proximal end 508 of the tube 504 is disposed proximal of the juncture of the extension 502 with the multifilar shaft 501. The tube 504 enters the extension 502 and proceeds through the distal end of the balloon 506. Thus, this embodiment comprises a distal extension of the shaft (in this case the coaxial extension 502) and the wire guide lumen structure 504, a portion of the wire guide lumen structure being coaxial within the distal extension, another portion of the wire guide lumen structure 504 being outside the shaft adjacent thereto. The embodiment illustrated in FIG. 5C does not have an extension. The balloon 506 is disposed on the distal end of the multifilar shaft 501. The proximal end 508 of the tube 504 is disposed proximal of the juncture of the extension 502 with the multifilar shaft 501 and is affixed to the exterior of the multifilar shaft 501. The tube 504 passes through the middle of the balloon 506 and proceeds through the distal end of the balloon 506. In each of the embodiments shown in FIGS. 5A-5C, the placement of the proximal end 508 of the tube 504 along the multifilar shaft 501 affects the flexibility of the shaft 501. Therefore, variation in the placement is useful in increasing or reducing flexibility as desired in other embodiments.

FIG. 6 illustrates one embodiment of a balloon catheter 600 having an elongate shaft 601 comprising a multifilar tube. An inflation balloon 602 is disposed near the distal end. FIG. 6A is an enlarged detail illustration of a middle section of the catheter 600. As can be clearly seen in FIG. 6A, the shaft 601 includes an external wire guide lumen 604 and an internal inflation lumen 606. As shown in FIG. 6A, this embodiment the catheter shaft 601 is coated with a PEBA coating 603. The coating 603 serves to reduce friction during introduction of the catheter shaft 601 and provides a seal to prevent leakage of inflation fluid from the inflation lumen 606 through the walls of the shaft 601. As can also be seen in FIG. 6A, the catheter shaft 601 tapers distally to a smaller diameter along the region 605.

FIG. 6B is an enlarged detail illustration of a distal section of the balloon catheter 600. As shown in FIG. 6B, the inflation lumen 606 opens into the inflation balloon 602, and the wire guide lumen 604 extends through the balloon 602 to the distal end 607. FIG. 6B includes an enlarged detail portion more clearly illustrating the relationship between the balloon 602 and the two lumens (604 and 606). In this embodiment, the balloon 602 and wire guide lumen 604 are mounted to the shaft 601 with a PEBA shrink sleeve 608. As shown in FIG. 6C, a cross-sectional view of the sleeve 608 has approximately a figure-eight shape before mounting. The sleeve 608 has two central apertures (610 and 612) to allow mounting the sleeve 608 over the wire guide lumen 604 and the shaft. In this embodiment, after the balloon 602 and wire guide 604 are assembled to the shaft 601 together with the sleeve 608, the sleeve 608 is heated to shrink and form to the assembly of shaft 601, balloon 602, and wire guide 604. FIG. 6D is a transverse cross section along line 6D-6D of FIG. 6B, and shows the finished configuration. The sleeve 608 forms to the shaft 601 and leaves open the inflation lumen 606 and the wire guide lumen 604.

Cross-lumen communication may be prevented. For example, the walls of the multifilar tube of the elongate shaft 601 may be porous, and pressure exerted on an inflation fluid in the inflation lumen 606 may urge inflation fluid into the wire guide lumen 604. According to one aspect, this may be prevented by lining the wire guide lumen 604 with a liner such as, for example, PTFE, although other materials may be used. Furthermore, an inner coating segment may be placed over the elongate shaft 601 beneath the proximal breach or side opening of the wire guide lumen 604. The inner coating segment may be, for example, PEBA. The inner coating segment may be implemented to alter flexibility in the area of the segment, for example to avoid abrupt changes in flexibility. In one embodiment, the proximal end of the segment terminates at about halfway through the taper and the distal end of the segment terminates just distal of the proximal breach or side opening of the wire guide lumen 604. According to another aspect, cross-lumen communication may be prevented by placing the coating 603 over essentially the entire length of the elongate shaft 601, and the sleeve 608 may subsequently be placed over the coating 603 and elongate shaft 601. According to yet another aspect, cross-lumen communication may be prevented by simply making the walls of the sleeve 608 thicker. A 0.001 inch (0.025 mm) wall thickness of the coating 603 or sleeve 608, for example, may be sufficient. As mentioned previously, the coating 603 and sleeve 608 may be PEBA or another suitable material. These principles may be implemented in other embodiments of the invention as may be desirable due to fluid being passed through or injected into one of the lumens.

Figure 7A:
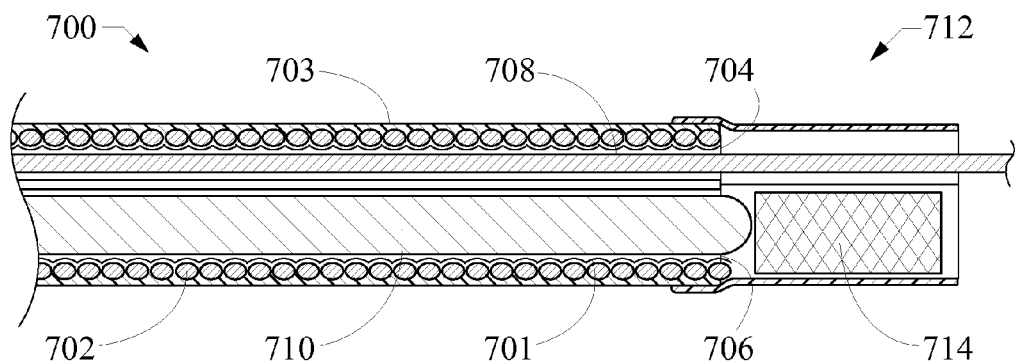
FIGS. 7A and 7B illustrate a cross-sectional view of another embodiment of a catheter device.
Figure 7B:
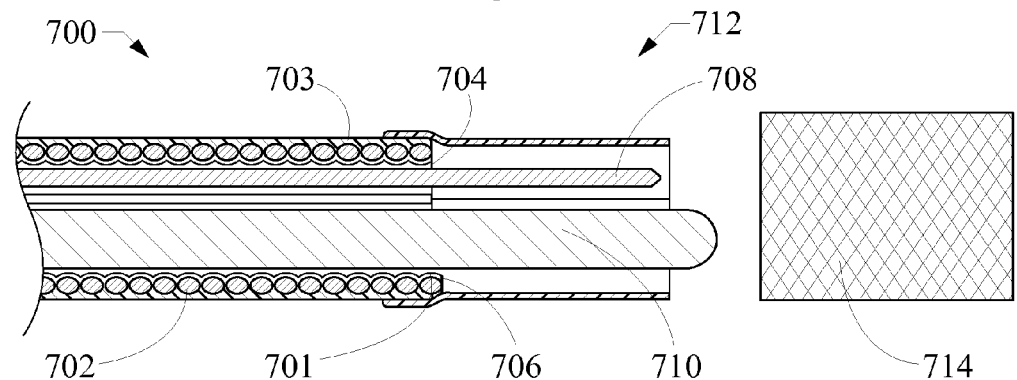

FIGS. 7A-7B illustrate a cross-sectional view of a portion of a catheter device 700 according to one aspect of the present invention. A shaft wall comprising multiple filars 702 includes an inner coating 701 and an outer coating 703, and surrounds a first lumen 704 and a second lumen 706. A wire guide 708 extends through the first lumen 702, and a stent-deployment shaft 710 extends through the second lumen 706. As shown in FIG. 7A, the catheter device 700 includes a distal extension 712 that houses a self-expandable stent 714. FIG. 7B illustrates the stent 714 having been pushed out of the second lumen 706 by the stent-deployment shaft 710 such that the stent 714 is deployed. Prior to deployment of the stent 714, the wire guide 708 is typically retracted into the shaft wall or lumen 704 so as not to interfere with deployment of the stent 714.

Figure 8:
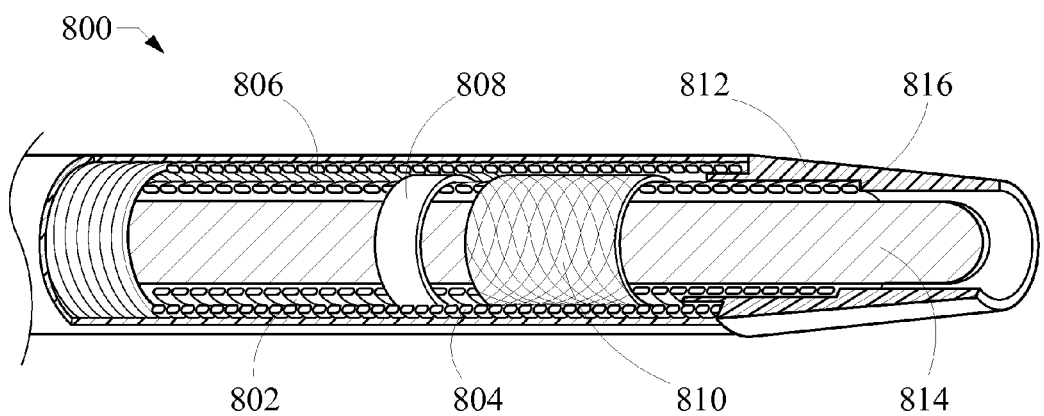
FIG. 8 illustrates a partial cross-sectional view of yet another embodiment of a catheter device.

FIG. 8 illustrates a partial cross-sectional view of another embodiment of a catheter device 800, including a self-expanding stent 810. The catheter device 800 has a central lumen 802 surrounded by a first, outer tubular multifilar body 804. A second, inner multifilar cable tube is coaxially disposed in the central lumen 802 for use as a pusher 806. The pusher 806 has a protruding engagement surface 808 for pushing the self-expanding stent 810 out of the central lumen 802 or for holding the stent 810 as the outer tubular multifilar body 804 is being pulled in a proximal direction. A tapered tip 12 is mounted on the distal end of the pusher 806, and provides a minimally traumatic leading surface for the catheter device 800. A wire guide 814 extends through a central wire guide lumen 816 of the pusher 806. Optionally, apertures (not shown) may be provided through the side of the outer tubular body 804 and the pusher 806 to permit the wire guide 814 to exit the central lumen 802 and the wire guide lumen 816 at an intermediate location. The self-expanding stent 810 is adapted to be deployed when a user retracts the outer tubular body 804 proximally while holding the pusher 806 substantially in place. The protruding engagement surface 808 of the pusher 806 holds the self-expanding stent 810 substantially in place while the outer tubular body 804 is withdrawn from around it. Once the stent 810 is deployed, the pusher 806 and wire guide 814 are withdrawn, leaving the stent 810 in the position where it was deployed.

FIGS. 9-9E illustrate one embodiment of a balloon catheter device 900 having an elongate multifilar tube shaft 901 and being configured for use in a short-wire application using a wire guide. An inflation balloon 902 is disposed near the distal end of the device 900 and is sealed thereto. FIG. 9A is an enlarged detail illustration of an intermediate section of the catheter 900. As shown in FIGS. 9 and 9A, the catheter 900 includes an internal shaft lumen 906 and an external wire guide lumen 904a that is housed by a wire guide tube 904. As shown in FIG. 9A, the shaft 901 may be coated with a PEBA or other coating 903. In one aspect, the coating 903 may help to reduce friction during introduction of the catheter shaft 901 and provide a seal that prevents leakage of inflation fluid from the shaft lumen 906 through the multifilar wall of the shaft 901. Those of skill in the art will appreciate that a coating 903 may be disposed on the exterior of the shaft 901, or it may be disposed as a lining/coating on the interior/lumenal surface of the shaft lumen 906, or both. As is also depicted in FIG. 9A, the catheter shaft 901 tapers distally to a smaller diameter along a narrowing transitional region 905, which provides for a distal shaft portion that is more flexible than the proximal shaft portion. An increased distal flexibility may allow the catheter device 900 to be more readily navigated through tortuous passages.

FIG. 9B is an enlarged detail illustration of a distal section of the balloon catheter 900. As shown in FIG. 9B, both the shaft 901 and the wire guide lumen tube 904 extend through the balloon 902 to the distal end 907. The distal end of the shaft 901 may be provided with a sealing tip 909, which preferably has an atraumatic distal profile. FIG. 9C shows an enlarged detail portion of FIG. 9B to illustrate the relationship between the balloon 902 and the wire guide and shaft lumens (904a and 906). The portion of the shaft 901 inside the balloon 902 does not include the coating 903, and the filars forming the wall of the shaft 901 do not form a fluid-tight barrier. As a result, and as indicated by arrows 919, the shaft lumen 906 may be used effectively as an inflation lumen because inflation fluid introduced therethrough can pass through an intralumenal portion the multifilar wall of the shaft 901 (inside the lumen of the balloon 902) to inflate the balloon 902. However, the wire guide lumen tube 904 most preferably is configured not to allow fluid communication from the shaft lumen 906 or the lumen of the balloon 902. Specifically, the wire guide lumen tube 904 is configured such that inflation fluid passing through the wall of the shaft 901 into the lumen of the balloon 902 will not escape through the wire guide lumen 904a. As is also shown in this embodiment, the shaft 901 extending through the length of the balloon 902 may provide longitudinal support for the balloon 902.

As is also shown in this embodiment, the balloon 902 and wire guide lumen tube 904 may be mounted to the shaft 901 with a shrink sleeve 908. As shown in FIG. 9D, the sleeve 908 has approximately a figure-eight shape before mounting. The sleeve 908 includes two central apertures (910 and 912) to allow for mounting the sleeve 908 over the wire guide lumen tube 904 and the shaft 901. In this embodiment, after the balloon 902 and wire guide tube 904 are assembled to the shaft 901 together with the sleeve 908, the sleeve 908 may be heated to shrink and form to the assembly of the shaft 901, balloon 902, and wire guide tube 904. FIG. 9E is a transverse cross section view along line 9E-9E of FIG. 9C that shows the finished configuration. The sleeve 908 forms to the exterior surface of the shaft 901 and leaves open the shaft lumen 906 and the wire guide lumen 904a. As is shown in FIG. 9A, the sleeve 908 may extend over and proximally beyond the wire guide tube 904. Accordingly, a wire guide aperture 914 may be skived out or otherwise created to provide access to the wire guide lumen 904a. Those of skill in the art will appreciate that, in lieu of using a sleeve, the coating 903 may be extended to contact the wire guide tube 904 and/or the balloon 902 to provide a seal of the coating 903 with the wire guide tube 904 and/or the balloon 902, or that other means for securing the wire guide tube 904 and balloon 902 to the shaft 901 may be used within the scope of the present invention.

Figure 10:
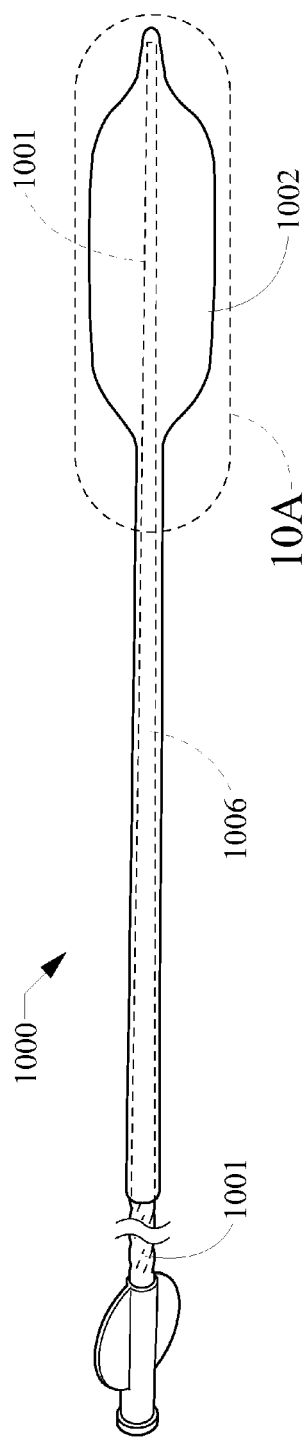
FIGS. 10-10A show yet another catheter device embodiment.
Figure 10A:
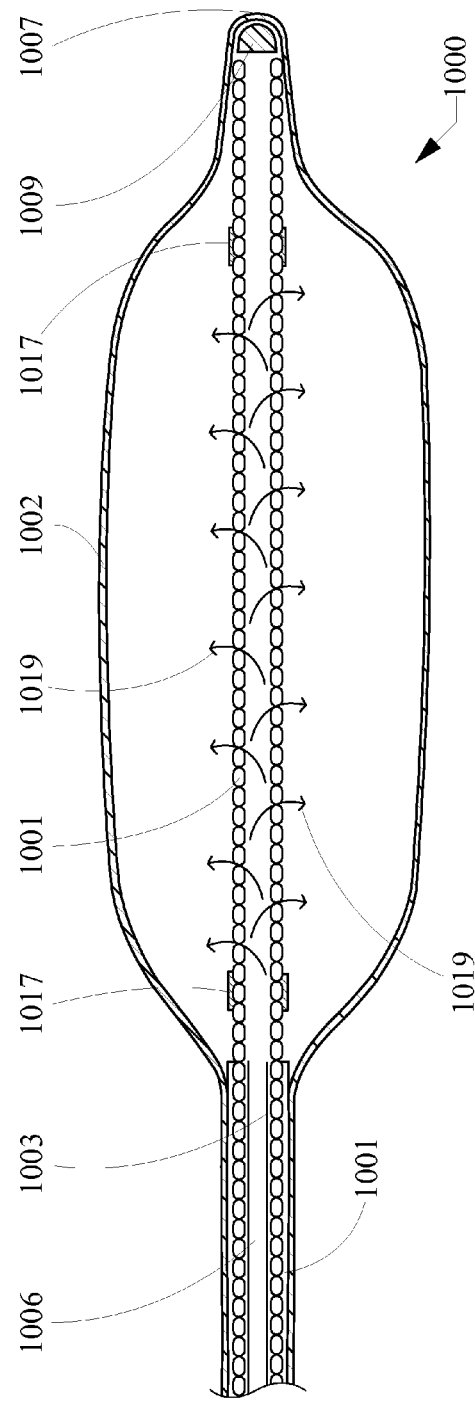

FIGS. 10-10A illustrate an embodiment of a balloon catheter device 1000 having an elongate multifilar tube shaft 1001 and being configured for use without a wire guide. In one aspect, the embodiment of FIG. 10 may be configured such that it may be manipulated during navigation in the same manner as a wire guide. An inflation balloon 1002 is disposed near the distal end of the device 1000 and is sealed thereto in a manner that forms a continuously sealed length of the shaft lumen 1006 proximal of the balloon 1002 in cooperation with an internal shaft lumen coating 1003. In one aspect, the coating 1003 may help to provide a seal that prevents leakage of inflation fluid from the shaft lumen 1006 through the multifilar wall of the shaft 1001. The catheter shaft 1001 may include a tapering diameter that is smaller distally than proximally and provides for a distal shaft portion that is more flexible than the proximal shaft portion while maintaining desirable pushability and trackability.

FIG. 10A is an enlarged detail illustration of a distal section of the balloon catheter 1000. As shown in FIG. 10A, the shaft 1001 extends through the balloon 1002 to the distal end 1007. The distal end of the shaft 1001 may be provided with a sealing tip 1009, which preferably has an atraumatic distal profile. The coating 1003 substantially covers the surface of the shaft lumen 1006 through the proximal length of the shaft 1001 and terminates near the proximal end of the balloon 1002 such that an intralumenal portion of the shaft 1001 (inside the interior space of the balloon, at least part of which forms a lumen of the balloon 1002) does not include the coating 1003, and the filars forming at least that portion of the wall of the shaft 1001 do not form a fluid-tight barrier. As a result, and as indicated by arrows 1019, the shaft lumen 1006 may be used effectively as an inflation lumen because inflation fluid introduced therethrough can pass through the multifilar wall of the shaft 1001 to inflate the balloon 1002. Those of skill in the art will appreciate that a coating may be used on the shaft exterior in addition to or instead of the lumenal shaft coating 1003, and that, if a coatings are present on both the interior and exterior shaft surfaces, each coating may include the same or different materials as the other coating. In this embodiment, the shaft 1001 also provides longitudinal support for the balloon 1002. The shaft portion disposed within the balloon 1002 may include a pair of radio-opaque markers 1017 configured to allow a user to fluoroscopically visualize the position of the balloon 1002. Suitable radio-opaque markers may include swaged metal (such as, for example, stainless steel, platinum, gold) or a polymer infused with barium or another radio-opaque material.

In one preferred embodiment, a balloon catheter device such as the balloon catheter 1000 lacking an external wire guide structure may be constructed such that it may function similar to a wire guide. Specifically, the catheter 1000 may be configured such that it has a small outer diameter, is sufficiently flexible to pass through a tight curvature or tortuous passageway, and has pushability and trackability sufficient to be navigated through such tightly curved and/or tortuous pathways in the same manner as a wire guide, thereby obviating the need for a separate wire guide. Those of skill in the art will appreciate that a preferred outer diameter will be different for different applications, but the outer diameter a catheter embodiment configured for use in peripheral blood vessels may be in the range of about 0.040-0.055 inches, and that the outer diameter may differ along the length of the catheter embodiment.

In some embodiments, the shaft coating (if any) may be a material other than PEBA, and may include the same material or different material than the material in a mounting sleeve used to mount a balloon (for example, HDPE, PTFE, PET, polyurethane, polyimide, polyolefin, nylon, or any combination thereof). The balloon catheters of the present invention may be adaptable for use with expandable stents as is illustrated, for example, in FIG. 3B. In the embodiments described above, a flexible stylet (not shown) may be inserted through the inflation lumen for use during advancement/navigation of the catheter device to a desired location. Such a stylet may be used to increase stiffness and pushability in a circumstance where that is desirable (such as, for example, if the catheter is being used to cannulate a lesion). Use of a stylet that is shaped (such as, for example, with a curve of up to about 70°) may also allow a user to reshape the distal end of the catheter shaft in a manner that may, for example, allow easier indication and navigation of branch vessels. A preferred stylet will not extend beyond the distal end of the catheter device.

Figure 11:
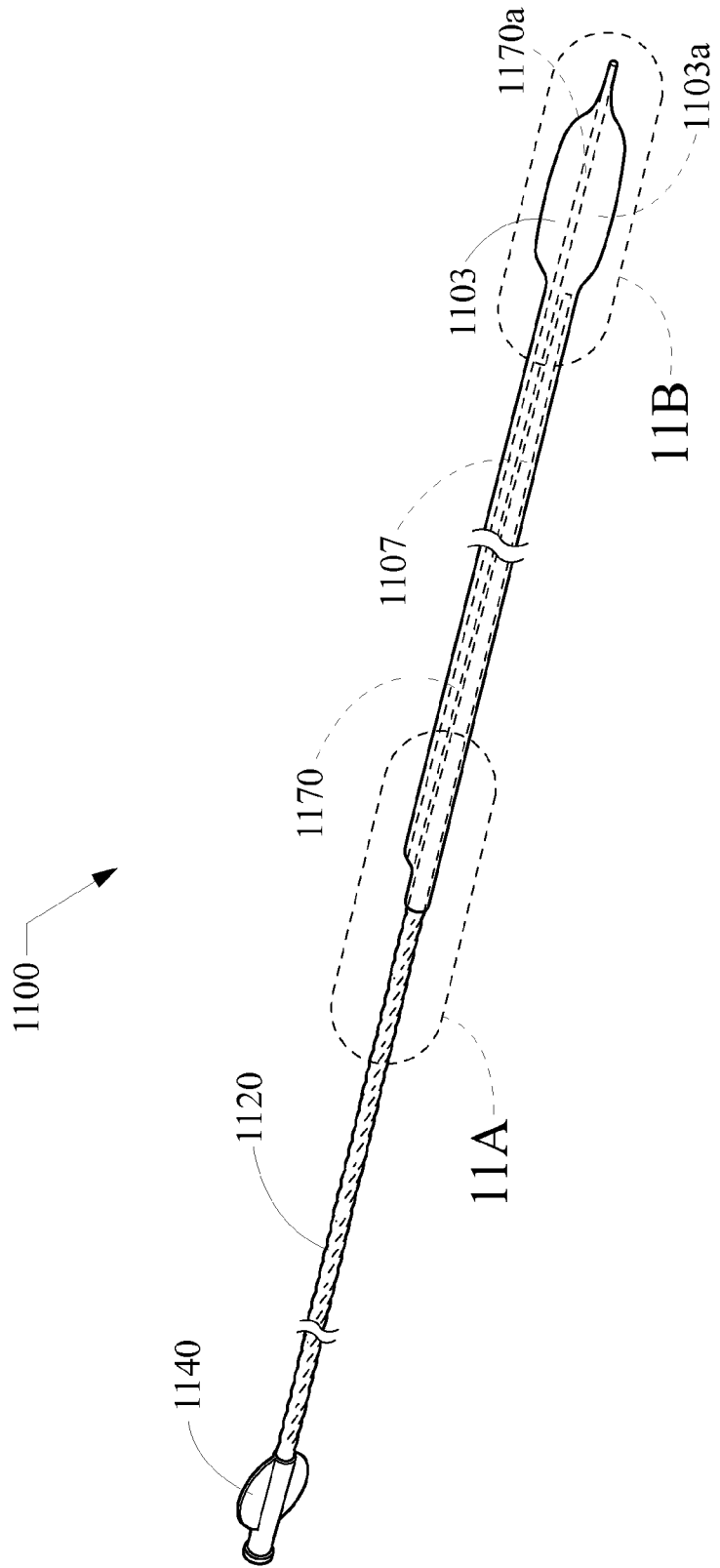
FIG. 11 is a side view of a multifilar catheter device having a distal wire guide lumen structure and an inflation balloon.
Figure 11A:
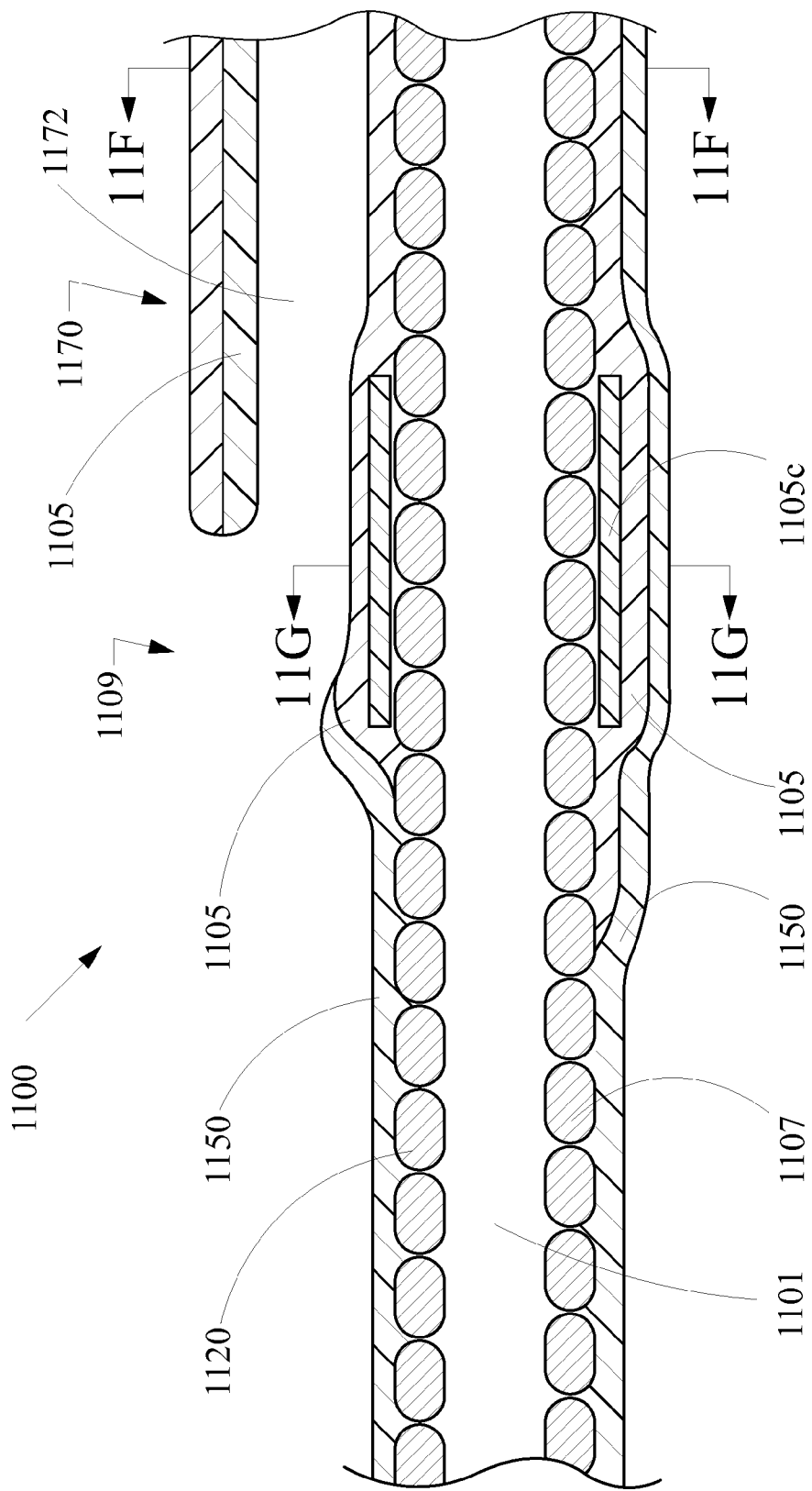
Figure 11F:
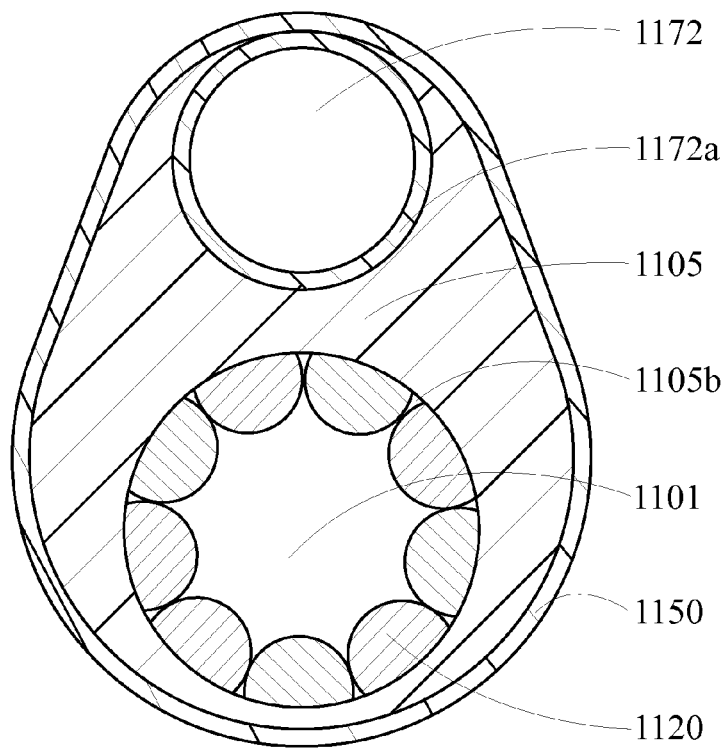
Figure 11G:
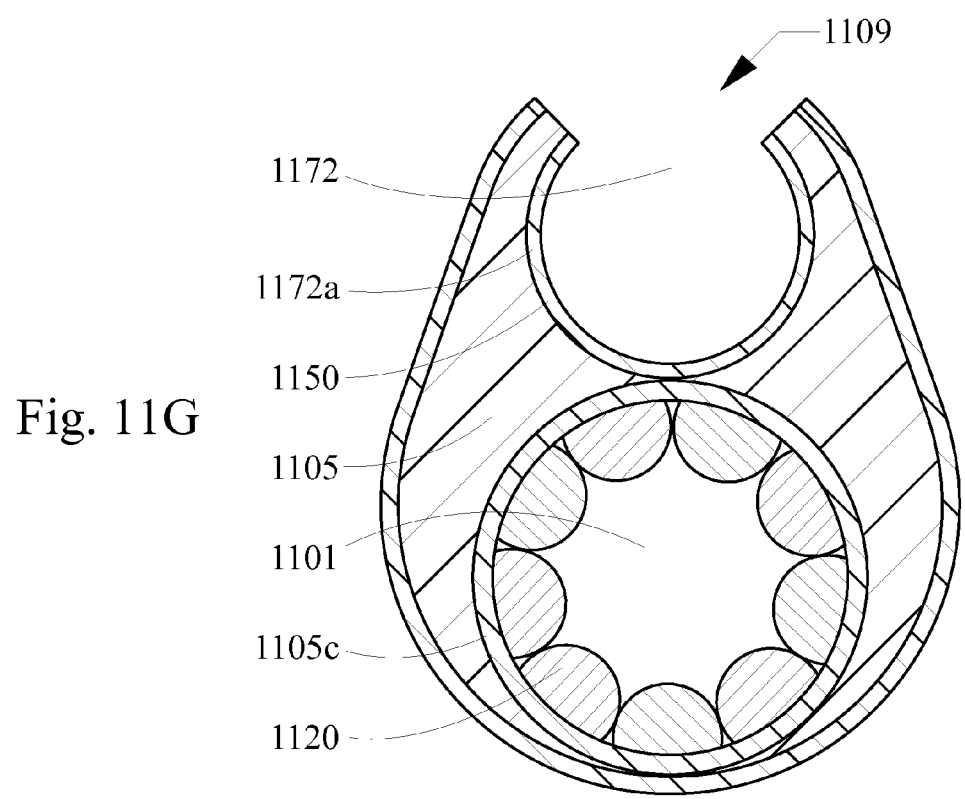

Another balloon catheter device embodiment 1100 is shown with reference to FIGS. 11-11G. The catheter device 1100 includes an elongate shaft 1107 including a monolayer multifilar tube 1120. An inflation balloon 1103 is disposed near the distal end of the device. A hub 1140 is disposed adjacent the proximal end of the device. FIG. 11A is an enlarged detail illustration of a distal-middle portion of the device 1100, showing a magnified longitudinal section view that includes a proximal portion of a wire guide lumen structure 1170 configured for use of the device in a short wire guide configuration. The wire guide lumen structure 1170 includes a wire guide lumen 1172 that extends substantially parallel with an inflation lumen 1101 of the shaft 1107.

In the illustrated embodiment, substantially the entire length of the shaft 1107 may include an outer layer 1150 as a coating. A preferred coating is a thermoplastic polymer such as, for example, a polyester or polyether block amide (e.g., PEBA®). A preferred coating will provide a desirable lubricity profile that exhibits low friction during introduction of the device through, for example, a blood vessel. A preferred coating will also provide a fluid-tight seal configured to prevent leakage of pressurized inflation fluid (for example, at pressures in a normal operating range up to about 8-14 atm, and preferably configured to prevent leakage at pressures exceeding normal ranges, for example, up to or exceeding about 27 atm).

A preferred catheter shaft 1107 tapers from a greater proximal outer diameter (such as, for example, about 0.048 to about 0.052 inches) to a lesser distal diameter (such as, for example, about 0.044 to about 0.040 inches). Those of skill in the art will appreciate that the lesser distal diameter may present improved trackability for navigation of tortuous passages.

As is shown in FIGS. 11B and 11C (which is an enlarged detail view of FIG. 11B), the inflation lumen 1101 of the catheter device 1100 is open to and provides fluid communication with the balloon lumen 1103a of the balloon 1103. A distal portion 1170a of the wire guide lumen structure 1170 including the wire guide lumen 1172 also extends through the balloon lumen 1103a and through the distal end of the balloon 1103 to a distal tip 1104. The distal end portion 1170a of the wire guide lumen structure 1170 preferably is very flexible (high trackability), and it may provide an advantage in directing the device 1100 along a wire guide (not shown) through particularly tortuous passages. FIG. 11B also shows the attachment of the balloon 1103 to the device 1100. Those of skill in the art will appreciate that, in another embodiment within the scope of the present invention, the balloon 1103 may be attached to the tube 1120 and configured such that the distal wire guide lumen structure portion 1170a extends exterior (of the balloon lumen 1103a) and adjacent the balloon 1103.

FIG. 11D shows a transverse cross-section of a dual-lumen thermoset sleeve 1105, which has a generally figure-8 cross-section and includes an upper lumen 1105a and a lower lumen 1105b. The sleeve 1105 preferably is constructed of a thermoplastic binder material such as, for example, a polyolefin, polyester or polyether block amide (PEBA), or other appropriate polymeric material having thermoplastic materials suitable for helping to form the wire guide lumen structure 1170 and to attach it to the tube 1120. As depicted in FIGS. 11E-11F (each of which represents a transverse cross-sectional view along line 11E-11E of FIG. 11A), the upper lumen 1105a of the sleeve 1105 defines the wire guide lumen 1172. The wire guide lumen 1172 may include a wire guide lumen liner 1172a, which preferably is made of a lubricious polymer that can form a thin wall with high strength such as, for example, PTFE, polyethylene, polyimide, or a similar material. In one aspect, the liner 1172a may help prevent fluid from leaking from the inflation lumen 1101 through pores of the tube 1120 into the wire guide lumen 1172. Preventing inflation fluid from leaking out of the inflation lumen is preferable for at least the reason that a substantially patent fluid lumen is required to allow passage of inflation fluid at a pressure and rate desired for proper inflation and deflation of the balloon. In another aspect, the portion of the sleeve 1105 between the sleeve lumens 1105a and 1105b may be provided with a desired thickness such as, for example, about 0.001 inches to minimize the likelihood of cross-lumen communication between the inflation lumen 1101 and wire guide lumen 1172.

The lower lumen 1105b surrounds the tube 1120. The outer layer coating 1150 of the device may extend over and surround the exterior of the sleeve 1105. As shown in FIGS. 11E-11F, the thermoset sleeve 1105 has been heated to conform around the wire guide lumen 1172 and tube 1120. FIG. 11E shows the sleeve 1105 as having been formed with a round cross-section, and FIG. 11F shows the sleeve 1105 as having been formed with an out-of-round cross-section. The latter configuration is preferred when the device 1100 is to be used in conjunction with a guide sleeve (not shown) through which contrast fluid may be injected, because the out-of-round profile will more readily permit contrast fluid to flow through a circular-cross-section guide sheath lumen and around the sleeve 1105. However, it is preferable that the cross-sectional height not be greatly different than the cross-sectional width.

A wire guide aperture 1109 is described with reference to FIGS. 11A and 11G (which is a transverse cross-sectional view of FIG. 11A along line 11G-11G). In order to facilitate use of the catheter device 1100 in a short wire configuration, a wire guide aperture 1109 is provided near the proximal end of the wire guide lumen structure 1170. The wire guide aperture 1109 may be formed by skiving an opening through the outer layer 1150, upper surface of sleeve 1105, and (if present) wire guide lumen liner 1172a. This aperture 1109 will, for example, allow a wire guide (not shown) directed from the distal end 1104 through the wire guide lumen 1172 to exit. As described above, mounting the device 1100 onto a wire guide in this manner may facilitate rapid introduction and/or exchange of the device 1100 along the wire guide. In order to provide additional protection against cross-lumen leakage in the aperture region, an additional barrier 1105c may be provided around the circumference of the shaft 1107 along a shaft region adjacent the aperture 1109. The barrier 1105c preferably will be formed of a high-strength polymer that preferably is impermeable to inflation fluid such as, for example, a polyether block amide or similar material.

Example 1

Figure 12A:
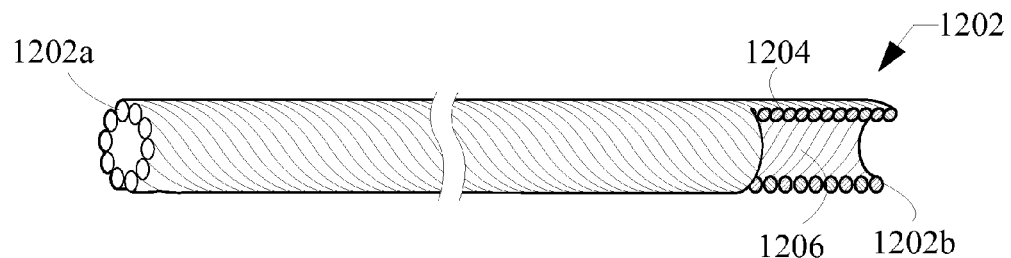
Figure 12B:
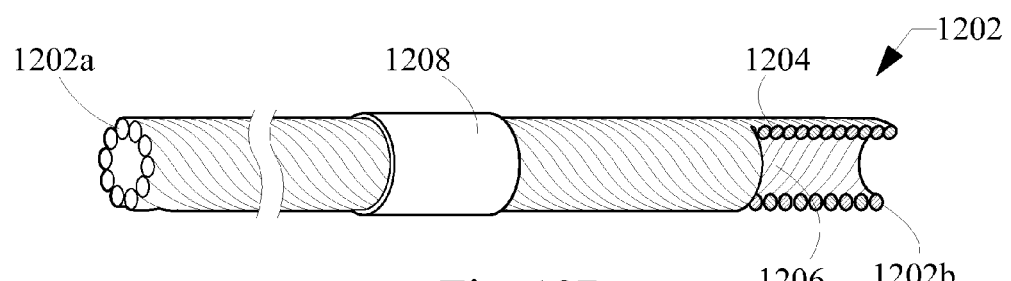

An exemplary method of making a wire-guided balloon catheter 1200 is described with reference to FIGS. 12A-12K. Those of skill will appreciate that this and other embodiments may be constructed using alternative methods within the scope of the present invention. As shown in FIG. 12A, a multifilar tubular shaft 1202 is provided, including a monolayer tubular shaft of ten filars coiled together to form a shaft wall 1204 defining a shaft lumen 1206. The shaft 1202 includes a proximal end 1202a and a distal end 1202b, and it has desirable pushability and trackability characteristics, with a structure that tapers from a proximal outer diameter of about 0.05 inches to a distal diameter of about 0.04 inches. (NOTE: FIGS. 12A-12K, along with all other figures of the present application, may not be drawn to scale). Next, as shown in FIG. 12B, a PEBA barrier sleeve 1208 is placed around a distal region of the shaft wall 1204 and heated to sealingly shrink around it (1204).

Figure 12C:
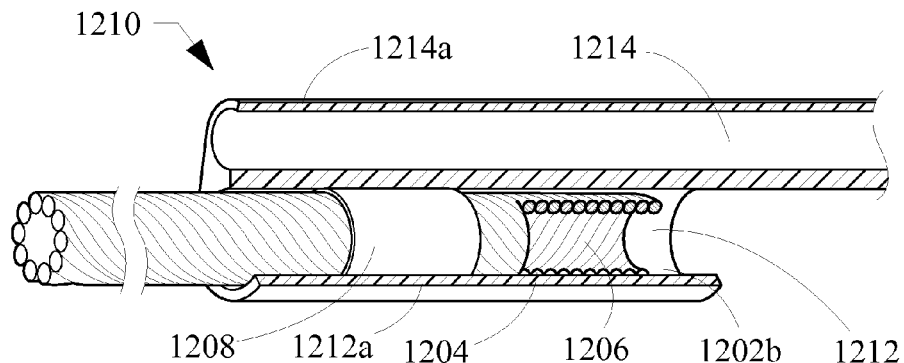

Then, as depicted in FIG. 12C, an elongate dual-lumen sleeve 1210 is provided. The dual-lumen sleeve 1210 includes a lower lumen 1212 and an upper (wire guide) lumen 1214. An upper lumen portion 1214a of the sleeve 1210 extends distally beyond a lower lumen portion 1212a of the sleeve 1210. FIG. 12C shows the dual-lumen sleeve 1210 as having been mounted onto the shaft wall 1204 of the shaft 1202 by sliding a distal portion of the shaft 1202 into the lower lumen 1212 until the distal shaft end 1202b is near the distal end of the lower lumen portion 1212a.

Figure 12D:
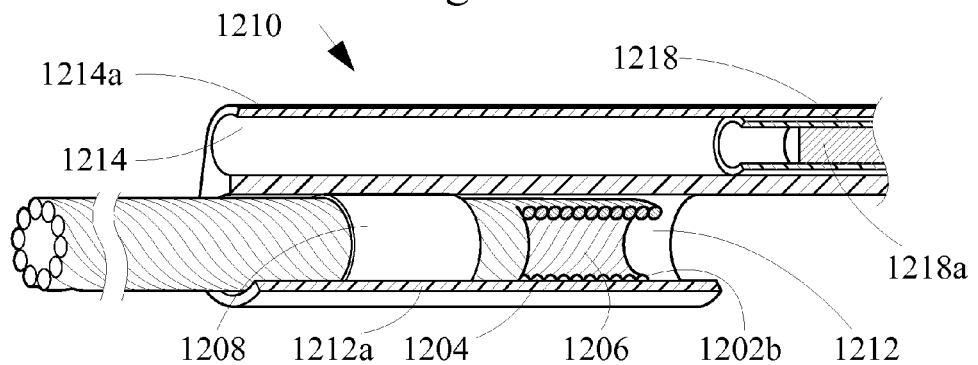
Figure 12E:
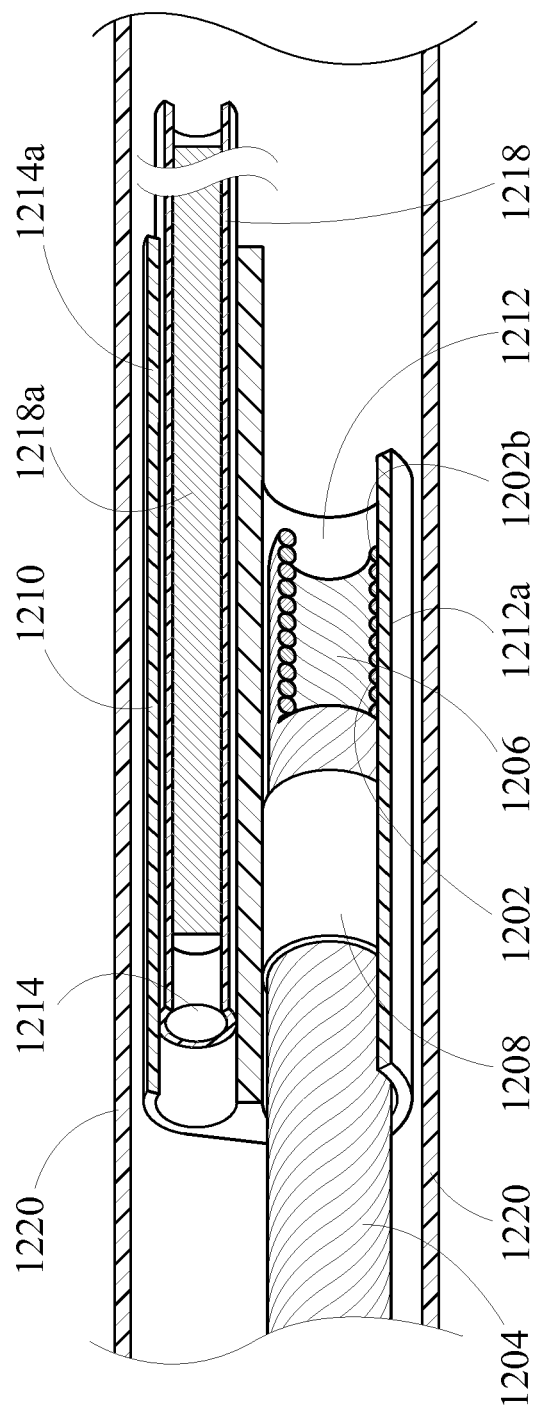
Figure 12F:
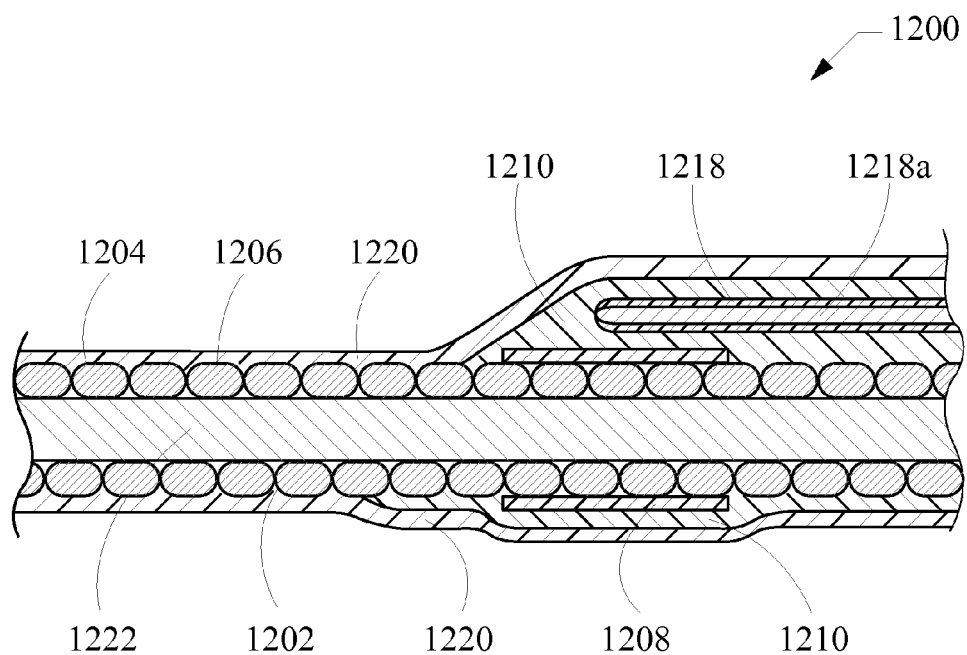

FIG. 12D shows a PTFE wire guide lumen liner 1218 provided on a first mandrel 1218a. The liner 1218 will be directed into the upper (wire guide) lumen 1214 until its (1218) proximal end is adjacent the proximal end of the upper (wire guide) lumen 1214. Next, as shown in FIG. 12E, a tubular PEBA thermoplastic sheath 1220 is directed over the entire length of the shaft 1202 such that it also encircles that portion of the dual-lumen sleeve 1210 around the distal region of the shaft 1202. Then, as illustrated in FIG. 12F, after the assembly is heated, the sheath 1220 shrinks around the shaft length to form a sealing coating 1220 along the length of the shaft 1202 and fusing the dual lumen sleeve 1210 to the shaft wall 1204 and the liner 1218. During the heat-shrink step, a second mandrel 1222 is provided through the shaft lumen 1206 to prevent it from becoming occluded by any coating material that may seep through the shaft wall.

Figure 12G:
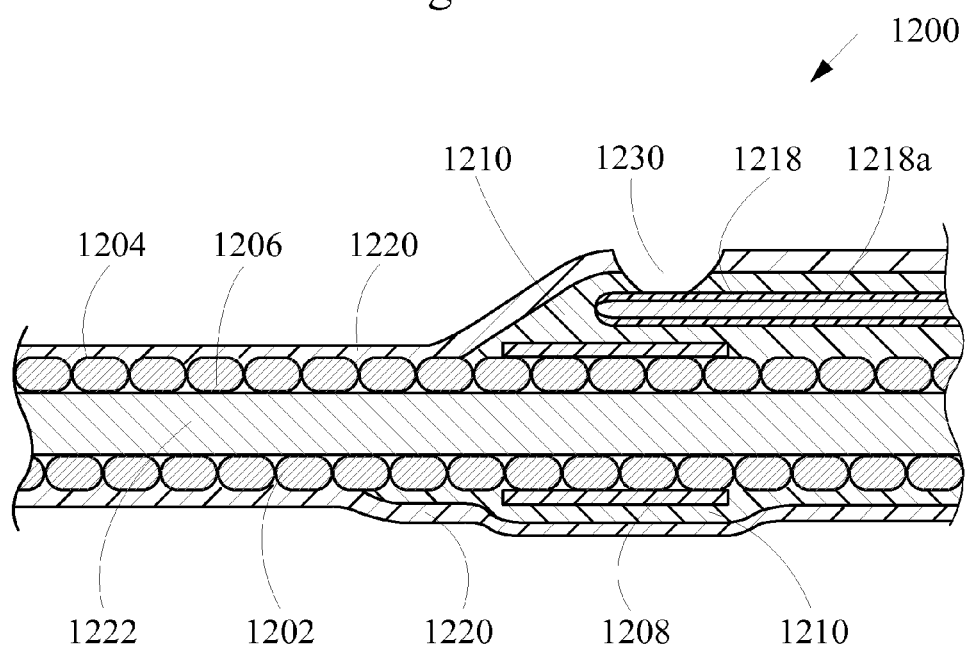
Figure 12H:
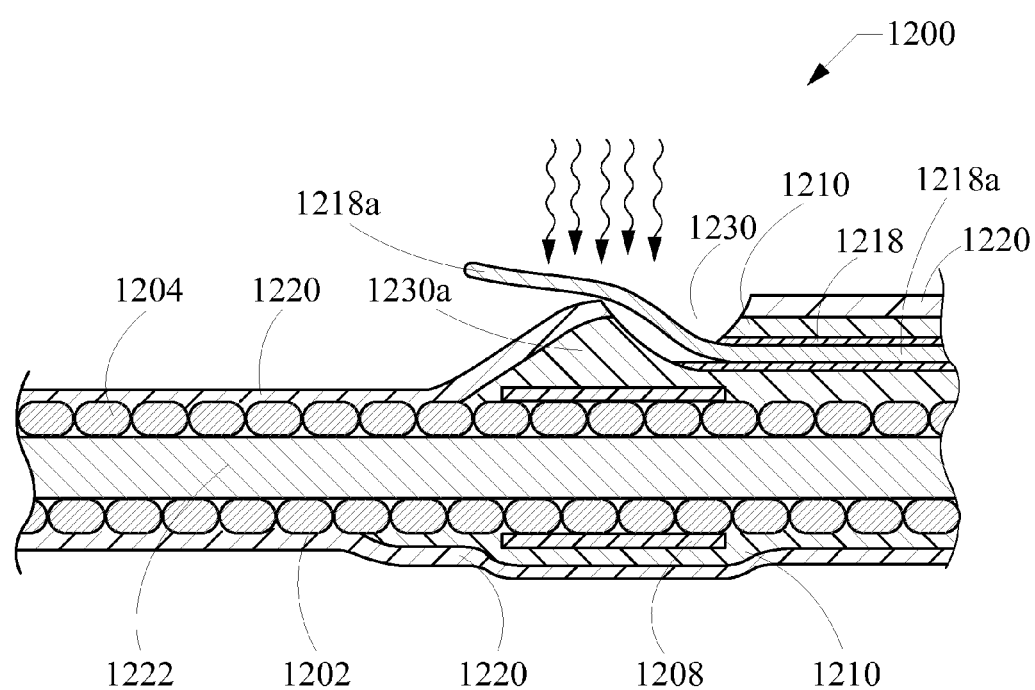

Next, as depicted in FIG. 12G, a wire guide aperture 1230 is skived near the proximal end of the upper (wire guide) lumen 1214 by cutting or otherwise incising through the sheath 1220, the sleeve 1210, and the liner 1218. FIG. 12H shows that the first mandrel 1218a (or a different mandrel, not shown) is directed through the wire guide aperture 1230 in a manner that compresses a portion of the dual lumen sleeve 1210 immediately proximal of the wire guide aperture 1230. The compressed region is heated and, as shown in FIG. 12J, substantially fuses to form a proximal ramped surface 1230a as a proximal portion of the wire guide aperture 1230.

Figure 12K:
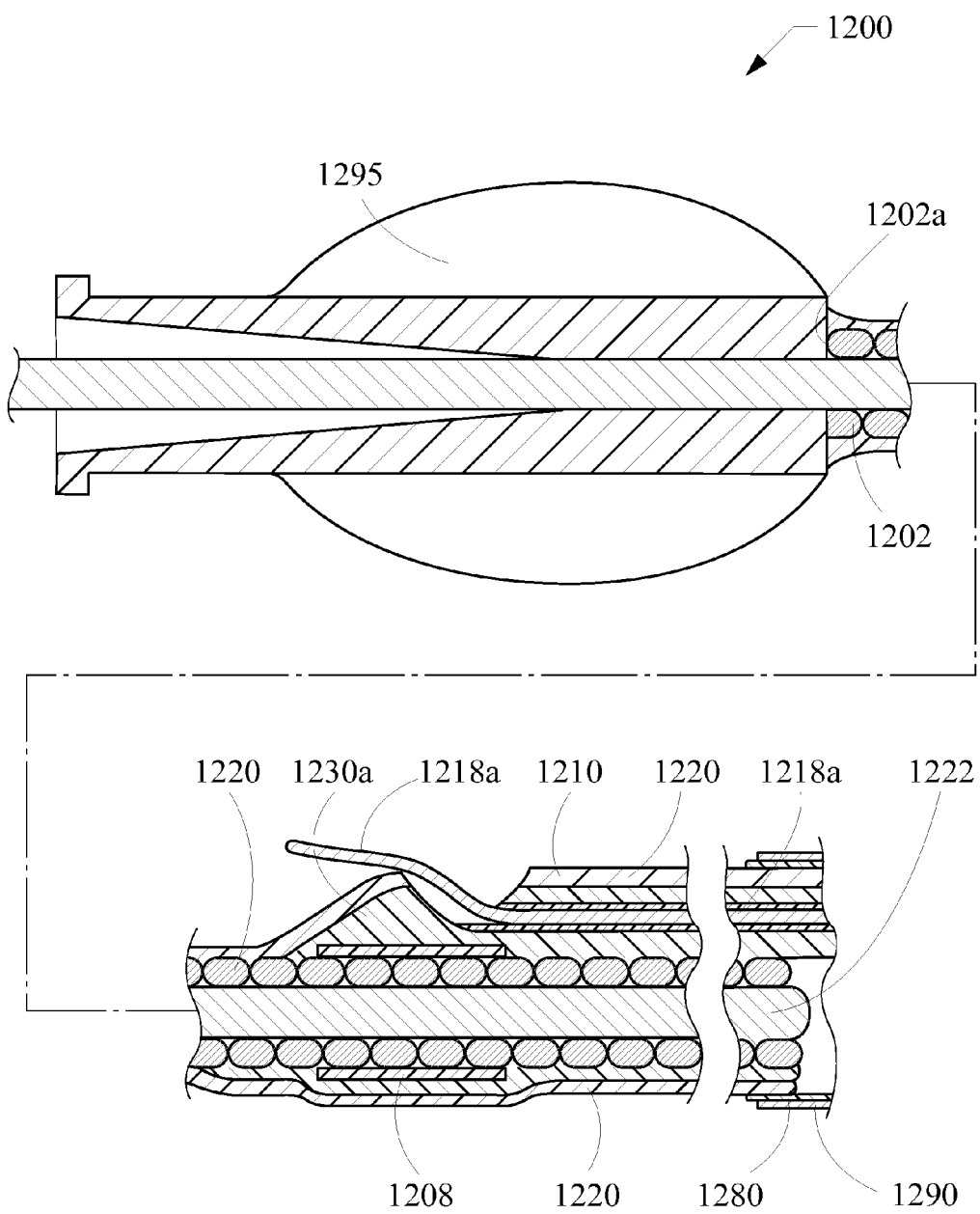
Figure 14:
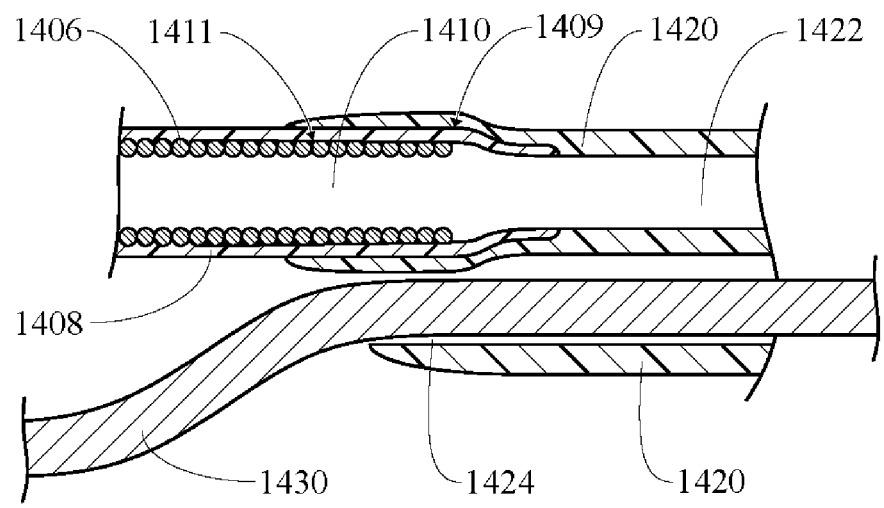
FIG. 14 shows one embodiment of a transition between the cable tube shaft portion and a polymer tube shaft portion of the catheter of FIG. 13.

As illustrated in FIG. 12I, the proximal end of a balloon 1280 is attached (preferably by a heat seal or equivalent means) to the assembly adjacent the distal shaft end 1202b such that the upper lumen portion 1214a of the sleeve 1210 extends through the lumen 1282 and distal end of the balloon 1280. The distal end of the balloon 1280 is sealed (also preferably by a heat seal or equivalent means) to the upper lumen portion 1214a of the sleeve 1210, which houses the wire guide lumen 1214. The PTFE wire guide liner 1218 does not need to extend completely to the distal end of the upper lumen portion 1214a of the dual-lumen sleeve 1210. The balloon 1280 can be compressed and folded, and—if desired—a stent 1290 mounted thereto as shown in FIG. 12J. And, as shown in FIG. 12K, a hub 1295 may be mounted to the proximal shaft end 1202a. In another embodiment of this method, the longitudinal shape of that upper lumen portion that is distal of the multifilar shaft may be modified to align generally with a longitudinal axis of that multifilar shaft or of the combined multifilar shaft and outer sleeve 1210 in a manner similar to that shown in FIG. 5C.

In another aspect of the present invention, it should be appreciated that, for many embodiments described herein, the multifilar tube may be substituted with a helically-cut or helically-scored hypotube (such as, for example, stainless steel or nitinol hypotube), collectively referred to herein as helically-scored hypotube. Helically-scored hypotube is well known in the catheter art, and those of skill in the art will appreciate that catheter embodiments including a tube of helically-scored hypotube rather than an elongate monolayer multifilar tube may be practiced within the scope of the present invention. For example, one embodiment may include an elongate helically-cut hypotube, said hypotube including a proximal tube end, a distal tube end, and a longitudinal tube lumen extending therebetween. In such an embodiment an inflatable balloon may be disposed adjacent the distal tube end such that a lumen of the balloon is in fluid communication with the longitudinal tube lumen, wherein the tube includes a substantially patent path of fluid communication between a proximal tube portion and the balloon lumen. Such an embodiment may also include a dual-lumen sleeve structure disposed adjacent the distal tube end, said dual-lumen sleeve structure comprising a first sleeve lumen and a second sleeve lumen, wherein the first sleeve lumen includes a wire guide lumen and extends distally beyond the distal tube end. The second sleeve lumen includes a tube-bonding lumen through which is disposed a tube portion adjacent the distal tube end. A coating may be provided that covers substantially the exterior surfaces of the tube and the sleeve structure, and provides a patent fluid communication path along the tube lumen between the proximal tube end and the balloon lumen. In particular, the balloon is connected near its proximal end to the tube and to the sleeve structure, and is also connected distally to the sleeve structure such that at least a portion of the sleeve structure extends through the balloon lumen. In this manner the first sleeve lumen extends distally beyond a distal end of the balloon. Furthermore, a wire guide aperture may be proximally disposed on the wire guide lumen and be configured to provide passage therethrough for a wire guide. Additionally, a wire guide lumen-lining layer may be provided in the wire guide lumen. Also, a sleeve structure may be provided around the hypotube adjacent the wire guide aperture in order, for example, to provide enhanced structural strength and to decrease the likelihood that inflation fluid may travel from the tube lumen to the wire guide lumen. This embodiment may also be used with a stent or other expandable device. Those of skill in the art will note that this embodiment may be understood and practiced, including a method of making the embodiment, with reference to FIGS. 11-12K, wherein helically-cut hypotube is used rather than a multifilar tube, and that other embodiments described herein may similarly be adapted for use with helically-cut hypotube within the scope of the present invention.

A different embodiment of a balloon catheter shown as a multifilar cable catheter 1400 configured for short wire/rapid-exchange use is described with reference to FIGS. 13-13C, 14, and 15. The catheter device 1400 includes a proximal-end hub 1402 with a fitting 1404 (e.g., a Luer-type fitting for an inflation fluid source). An elongate shaft including a proximal multifilar cable tube 1406 extends distally from the hub 1402. An intervening strain relief portion 1405 may be provided as well. The multifilar cable tube 1406 preferably is formed as a continuous monolayer or multi-layer tube of laterally-touching coiled filars, each having a length that does not cross over itself nor other filars. Specifically, it is preferably that adjacent filars of any individual layer are non-interlaced/non-overlapping (i.e., not braided, woven, interlaced or otherwise overlapping/engaging beyond a substantially lateral contact). Suitable multifilar tubing may be obtained, for example, from Asahi-Intecc (Newport Beach, Calif.) or from Fort Wayne Metals (Fort Wayne, Ind.). Materials and Methods of manufacturing suitable multifilar tubing are described in U.S. Pat. No. 7,117,703 (Kato et al.), which is incorporated herein by reference. This configuration of cable tubing 1406 provides desirable pushability and trackability. The tubing 1406 defines a fluid-patent multifilar tube lumen 1410 configured as the proximal portion of an inflation lumen. In some suitable configurations, filars of the multifilar tube may be swaged to create smooth inner and outer diameter surfaces of the tube formed thereby.

A jacketing material 1408 sealingly coats the outer surface of the cable tube 1406. The jacketing 1408 is clearly illustrated in FIG. 13A, which is a transverse cross section view of FIG. 13 along line A-A. The lumen-facing surface of the tube 1406 in FIG. 13A is shown as being swaged to provide a generally smooth surface for the lumen 1410, and those of skill in the art will appreciate that other interior and exterior portions of the tube 1406 may also be swaged in this or a similar manner. Suitable materials for the jacketing 1408 include heat-shrink tubing such as, for example, a polyether block amide barrier material (e.g., PEBA) that is thermoformed to the exterior of the cable tube to provide a sealing coating and maintain fluid patency of the cable tube 1406 during introduction of inflation fluid through the inflation lumen 1410. Other materials that may be used in the jacketing include HDPE, PTFE, PET, polyurethane, polyimide, polyolefin, nylon, or any combination thereof (including combinations with PEBA). In certain embodiments, it may be advantageous to roughen the external surface 1411 of the cable tube 1406 (e.g., by sanding, blasting, or any other technique that would roughen and/or otherwise increase the texture and/or surface area to enhance frictional contact between the jacketing 1408 and tube 1406). This roughening provides enhanced strength of attachment without affecting weight or diameter in the manner that adhesive or ancillary connectors would, while also being configured to provide the desirable trackability and pushability of these embodiments. The external tube surface 1411 is also shown as being swaged in a manner tapering distally, but it should be appreciated that the surface 1411 may be swaged in a substantially linear fashion parallel to the longitudinal axis of the tube, and that the inner tube diameter defining the lumen 1410 may also be swaged (including for any lengthwise portion of the tube 1406). Although the texture is not visible in the drawing, one or both of the surfaces 1406, 1411 may be roughened to enhance the connection with adjoining surfaces.

A distal portion of the elongate shaft is formed of a polymer shaft tube 1420 secured to the cable tube portion 1406. A proximal polymer tube end preferably is attached directly to the polymer barrier coating formed by the jacketing material 1408 adjacent the distal cable tube end. In certain embodiments, it may be advantageous to roughen the external surface 1409 of the jacketing material 1408 (e.g., by sanding, blasting, or any other technique that would roughen and/or otherwise increase the texture and/or surface area to enhance frictional contact between the jacketing 1408 and polymer shaft tube 1420), and at least one or more of the polymer tube end, cable tube end, and/or jacketing material may be roughened for this reason. The polymer tube 1420 preferably is formed from materials having a durometer that provides substantially similar flexibility, trackability, and pushability as the coated cable tube portion, but—in certain embodiments—the distal polymer tube portion may be more flexible than a more proximal cable tube portion. In this manner, the transition region, intermediate in the shaft length, where the coated cable tube portion ends and the polymer tube portion begins most preferably will not provide a flex point where kinking or bending is likely to occur in the manner of some prior catheter devices.

For example, a cable tube made of nitinol or stainless steel may have an outer diameter of about 20-100 mil (about 0.51-2.54 mm), with a preferred range of about 30-80 mil (about 0.76-2.03 mm) and an inner diameter about 20-80 mil (about 0.51-2.03 mm). In one example, one may begin with a 12-filar stainless steel cable tube having an outer diameter of 35 mil (0.89 mm) and swage it to 33 mil (0.84 mm), and provide it with a 4 mil (0.1 mm) wall liner, and a 21 mil (0.53 mm) inner diameter. The distal polymer shaft 1420 may be formed of nylon, PEBA, or blend of nylon with PEBA and PEBA heat-shrink (which should, for all purposes of this application be considered as included wherever PEBA is mentioned), polyethylene, or other suitable materials, preferably having a durometer of about 76D, and preferably is formed as an extruded or molded dual-lumen tubing. Stated differently, the polymer tube portion provides very similar properties as compared to the cable tube portion in the region immediately adjacent the cable tube portion. This construction provides cost savings in materials as well as providing a kink-resistant construction with desirable pushability and trackability. Two different embodiments of a transition region between the cable tube shaft portion and the polymer tube shaft portion are illustrated with reference to FIGS. 14 and 15, each of which is illustrated in a longitudinal section view along line X-X of FIG. 13.

The distal polymer tube portion of the elongate shaft of the device 1400 is configured as a dual-lumen catheter. In this manner, the overall device 1400 includes a proximal single-lumen cable tube catheter portion 1406 and a distal dual-lumen polymer catheter portion 1420. A transverse cross-sectional view of the transition region from the single to the dual-lumen portion is shown in FIG. 13B which is a transverse cross sectional view taken along line B-B of FIG. 13. A fluid-patent polymer tube inflation lumen 1422 of the polymer tube 1420 sealingly encompasses the distal end of the jacketed cable tube 1406. A wire guide lumen 1424 begins at an angled wire guide port 1426. A wire guide 1430 is shown extending through the wire guide lumen 1424 and the wire guide port 1426. The inflation lumen 1410 of the proximal cable tube portion of the device 1400 continues a path of fluid-patent communication into and through the distal polymer tube inflation lumen 1422, forming a continuous inflation lumen. A transverse distal cross sectional view of the polymer catheter portion 1420, distal of the single-lumen cable tube catheter portion 1406 is shown in FIG. 13C, which is taken along line C-C of FIG. 13. As shown therein, the inflation lumen portion may include a non-circular cross-section.

A balloon 1450 is secured at its proximal end to the polymer catheter portion 1420. The polymer tube inflation lumen 1422 terminates where the polymer catheter portion 1420 joins the balloon 1450. The polymer tube inflation lumen 1422 is in patent fluid communication with a balloon lumen 1452. An intact, fluid patent portion of the polymer catheter 1420 extends through the balloon lumen 1452, providing a continuation of the wire guide lumen 1424 to the distal end of the balloon 1450, which is shown with the wire guide 1430 extending therefrom. As shown in FIG. 13, radio-opaque marker bands 1435 preferably are included on or in the wire guide lumen portion of the polymer catheter 1420 that extends through the balloon lumen 1450. The marker bands 1435 preferably are oriented parallel with the ends of an intermediate expandable balloon region, such that a user can fluoroscopically determine the location of the balloon 1450 for desired deployment.

The construction of the transition between the cable tube shaft portion 1406 and the polymer tube shaft portion 1420 may be embodied in at least two different ways. A first embodiment is described with reference to FIG. 14, which is presented as a longitudinal section view along line X-X of FIG. 13. The cable tube 1406 is covered with a sealing polymer jacket 1408. The jacket material 1408 extends distally beyond a distal end of the cable tubing 1406, providing a smooth transition between the cable tube lumen 1410 and the polymer tube lumen 1422. The polymer tube 1420 preferably is heat-bonded together with the jacketed cable tube 1406 by inserting a mandrel-type component (e.g., a building wire) through the lumens of both components (1410, 1422), then inserting the distal end of the jacketed cable tube 1406 into the proximal end of the polymer tube inflation lumen 1422, then heating the joint to form a secure sealed connection (during which it is preferable to provide a mandrel-type component through the wire guide lumen 1424 to maintain its patency). Although FIG. 14 uses different cross-hatching patterns to show the "pre-bonding" structure of the jacketing 1408 and the polymer tubing 1420, the "post-bonding" structure preferably will have these components melted together such that their structure will be relatively seamless. For purposes of illustration, the outer diameter of the distal polymer portion of the device 1400 is shown as being significantly greater than the proximal cable catheter portion, but it preferably will have an outer diameter that is nearly the same as, or only slightly greater than that of the proximal portion. The proximal end of the polymer catheter section 1420 preferably tapers slightly to present an atraumatic profile that will be easily navigable in proximal and distal directions through other lumens (e.g., body lumens, tool lumens such as of an introducer or endoscope).

A second embodiment of the transition region is described with reference to FIG. 15, which is presented as a longitudinal section view along line X-X of FIG. 13. The cable tube 1406 is covered with a sealing polymer jacket 1408. The jacket material 1408 terminates at the distal end of the cable tubing 1406, providing a smooth transition between the cable tube lumen 1410 and the polymer tube lumen 1422. The polymer tube 1420 preferably is heat-bonded together with the jacketed cable tube 1406 by inserting a mandrel-type component (e.g., a building wire) through the lumens of both components (1410, 1422), then inserting the distal end of the jacketed cable tube 1406 into the proximal end of the polymer tube inflation lumen 1422, and heating the joint to form a secure sealed connection (during which it is preferable to provide a mandrel-type component through the wire guide lumen 1424 to maintain its patency). The direct attachment between the polymer tube inflation lumen 1422 and the jacket of the cable tube 1406 preferably is a heat-set attachment substantially fusing the two together. This construction provides a smooth internal diameter of the inflation lumen that is substantially consistent between the cable tube lumen 1410 and the polymer tube lumen 1422. (And, it should be appreciated that, although the drawing figure uses different cross-hatching to show the different components, they may be constructed of the same materials and form a seamless, continuous layer).

Figure 15:
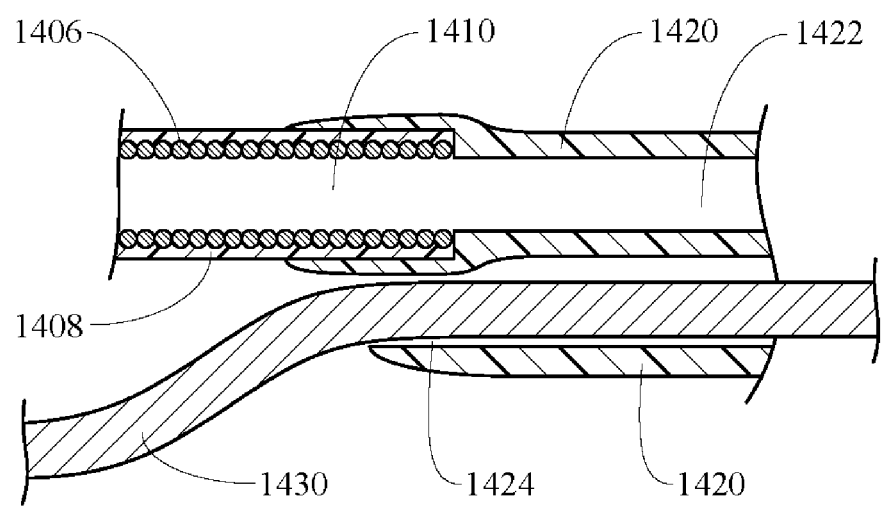
FIG. 15 shows another embodiment of a transition between the cable tube shaft portion and a polymer tube shaft portion of the catheter of FIG. 13.

Although FIG. 15 uses different cross-hatching patterns to show the "pre-bonding" structure of the jacketing 1408 and the polymer tubing 1420, the "post-bonding" structure preferably will have these components melted together such that their structure will be relatively seamless. For purposes of illustration, the outer diameter of the distal polymer portion of the device 1400 is shown as being significantly greater than the proximal cable catheter portion, but it preferably will have an outer diameter that is nearly the same as, or only slightly greater than that of the proximal portion. The proximal end of the polymer catheter section 1420 preferably tapers slightly to present an atraumatic profile that will be easily navigable in proximal and distal directions through other lumens (e.g., body lumens, tool lumens such as of an introducer or endoscope).

The cable tube 1406 and/or the polymer tube 1420 may be tapered to have a smaller distal outer diameter and increase flexibility. The durometer of the polymer tube portion 1420 may be selected such that it provides flexibility, trackability, and pushability that are substantially the same as the proximal cable tube portion 1406 (together with its jacket 1408). The wire guide aperture 1426 may be positioned near, but proximal of the distal end of the cable tube portion 1406. The durometer of the distal polymer tube portion 1420 may be selected such that its flexibility, trackability, and pushability are substantially the same as the proximal cable tube portion 1406 when a wire guide is present through the wire guide lumen 1424. Those of skill in the art will appreciate that less material may be used in this latter construction, thereby presenting a cost savings, while providing a catheter device that, as used, provides a substantially consistent flexibility, trackability, and pushability along its entire length during its actual use conditions when it is introduced along a wire guide, or that may be constructed to provide enhanced flexibility nearer the distal end. The balloon 1450 preferably is heat-sealed or attached by adhesive to the polymer tube 1420. The balloon may be constructed of essentially the same polymer as the polymer tube, such that it can be fused seamlessly with the polymer tube.

In certain preferred embodiments of a multifilar cable balloon catheter 1400, the distal polymer dual-lumen portion may have an outside diameter of about 45 mil (about 1.14 mm) with an inside/lumen diameter of about 21 mil (about 0.53 mm) for the inflation lumen and an inside/lumen diameter of about 18 mil (about 0.46 mm) to about 21 mil (about 0.53 mm) for the wire guide lumen. As is described with reference to other embodiments above, the cable tube portion and/or the polymer tube portion may be tapered from a larger proximal diameter to a smaller distal diameter to enhance the navigability of the distal portion through more tortuous passages.

In certain embodiments, it may be desirable to provide a large inflation lumen through the catheter body portions to supply fluid communication with a balloon lumen that will provide for desirably short inflation and deflation times during a procedure using a balloon catheter. The embodiments described above may provide this, but the cable tube proximal shaft (e.g., tubing 1406) may limit the flow rate therethrough as its jacketed outer diameter must fit into the flow-rate-optimized half-round lumen of the distal lumen portion (see, e.g., upper/inflation lumen 1422 of dual-lumen portion 1420 in FIG. 13C, which inflation lumen is in fluid communication with balloon lumen 1452). In other words, the outer diameter of the overall device is limited by the anatomy through which it will travel such as, for example, blood vessels or other body passages. This restricts the available internal diameter of the inflation lumen, particularly when a wire guide lumen is also provided. The transitional portion at the distal end of the cable tube portion of some catheter embodiments will have an internal diameter that is limited as a "choke point" of sorts. A structure and method is described below for providing attachment of a proximal jacketed multifilar cable tube having a larger internal diameter to a dual-lumen connector member (e.g., similar and/or analogous to polymer tube 1420 shown and described above). In this manner, a generally circular cross-section lumen of a proximal alloy tube may provide about the same (that is, slightly greater or less, exactly the same, substantially the same, or very nearly the same) cross-sectional area as a flow-optimized lumen of a distal inflation lumen of a dual-lumen catheter portion. Regardless of the size and contours of cross-sectional area provided, it will be preferable that the flow rate provided by the proximal inflation lumen will provide the same or a similar flow rate as the distal inflation lumen.

In one embodiment of a balloon catheter 1500, shown in FIGS. 16A-16B, a cable tube 1506 is provided. It preferably is sized such that its inflation lumen 1510 will provide for a flow-rate closely similar to the flow-rate provided by flow-rate-optimized half-round lumen 1522 (see, e.g., lumen 1422 in FIG. 13C) of the distal dual-lumen portion 1520. In order to avoid sacrificing flow rate-consuming space of the distal inflation lumen 1522, a cannula configured as a short thin-walled connector tube 1523 is provided. As shown in FIG.

16B, the thin-walled connector tube 1523 is configured for insertion into the inflation lumen 1522 of the distal dual-lumen tube 1520. When the catheter 1500 is assembled as shown in FIG. 16B, a patent path of fluid communication is provided between the cable tube inflation lumen 1510 and the distal member inflation lumen 1522. The cable tube 1506 has a larger outer diameter and inner diameter in proportion to the distal member inflation lumen 1522 when compared—for example—with the embodiments shown in FIGS. 14-15. As such, in this embodiment (and those of FIGS. 17-19B) the inner diameters of the cable tube 1506 and the distal inflation lumen 1522 are more similar and provide for more rapid flow during inflation and/or deflation of a balloon.

The distal dual-lumen portion 1520 is shown with a wire guide lumen 1524, illustrated with a wire guide 1530 disposed slidably therethrough. The thin-walled connector tube 1523 may be fused to the inner diameter of the cable tube lumen 1510, but preferably is laser welded at the distal end of the cable tube body 1506. A distal portion of the thin-walled connector tube 1523 may be roughened or otherwise treated to increase its surface area and/or frictional profile to improve its bonding with the jacketing 1508 and/or the distal dual-lumen tube member 1520. That distal member 1520 may be constructed of heat-shrink PEBAX, nylon-PEBAX blend, or another material that may be bonded (e.g., thermally by heat-shrink, with adhesive, or by some other connecting means) with the thin-walled connector tube 1523, and—in some embodiments—with a distal end portion of the proximal tube body 1506. The two portions shown may be fused and/or otherwise bonded together by, for example, adhesive, welding, soldering, an integrated or removable heat-shrink sleeve, or other attachment means that will provide a stable connection configured for use in a medical catheter.

In another embodiment of a balloon catheter 1700, shown in FIGS. 17-18C, a cable tube 1706 covered with jacketing material 1708 (such as, for example, heat-shrinkable PEBAX) is provided. It preferably is sized such that its inflation lumen 1710 will provide for a flow-rate closely similar to the flow-rate provided by flow-rate-optimized half-round lumen 1722 of the distal lumen portion 1720. Similar to the embodiment of FIGS. 16A-16B, a short thin-walled connector tube 1723 is provided. Also, similar to the embodiment shown in FIG. 16B, the thin-walled connector tube 1723 is configured for insertion into the inflation lumen 1722 of the distal dual-lumen tube 1720. When the catheter 1700 is assembled as shown in FIGS. 17B-18C, a patent path of fluid communication will be provided between the cable tube inflation lumen 1710 and the distal member inflation lumen 1722. The cable tube 1706 will generally have a larger outer diameter and inner diameter in proportion to the distal member inflation lumen 1722 when compared—for example—with the embodiments shown in FIGS. 14-15. As such, in this embodiment, the inner diameters of the cable tube 1706 and the distal inflation lumen 1722 are more similar and provide for more rapid flow during inflation and/or deflation of a balloon (although it will be appreciated with the shape of the distal lumen 1722, that its major height/inner diameter may be less than the inner diameter of the proximal inflation lumen 1710 for the major lengths of each.

Figure 17C:
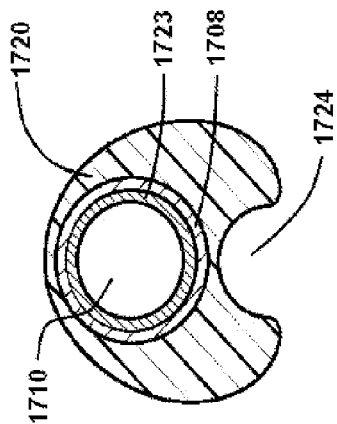
FIGS. 17C and 17D show, respectively, transverse section views along lines 17C-17C and 17D-17D of FIG. 17B.
Figure 17D:
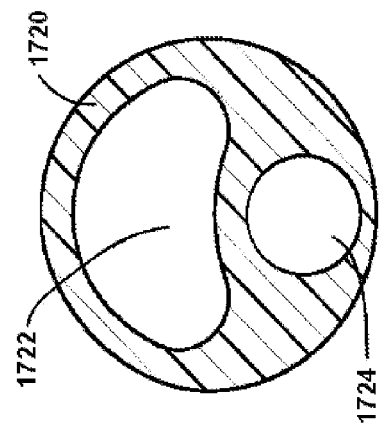

The distal dual-lumen portion 1720 is shown with a wire guide lumen 1724. A proximal portion of its inflation lumen 1722 is shown as having been expanded (e.g., by insertion of a mandrel, which may be heated). In this manner, a larger inner diameter "entry portion" of the distal inflation lumen 1722 is provided to receive the proximal catheter portion in a manner that provides a generally circular/cylindrical cavity without reducing the overall inner diameter that will be available for fluid flow in a final assembled catheter 1700. FIG. 17C, a transverse section view along line 17C-17C, shows the expanded/re-shaped "entry portion" of the distal lumen 1722, which has a generally circular cross-sectional geometry (not to scale, as the cross-sectional area of the proximal inflation lumen 1710 preferably will provide for the same or about the same flow rate as the cross-sectional area of the distal inflation lumen 1722), and FIG. 17D, a transverse section view along line 17D-17D, shows the unaltered portion of the distal lumen 1722, which has a generally follow-optimized half-round cross-sectional geometry. The cross sectional area of both may be about the same, and both will preferably provide about the same flow rate under the conditions of use associated with inflating and/or deflating a dilation balloon. The thin-walled connector tube 1723 preferably is fused to the distal end and/or the inner diameter of the cable tube lumen 1710. A distal portion of the thin-walled connector tube 1723 may be roughened or otherwise treated to increase its surface area and/or frictional profile to improve its bonding with the jacketing material 1708. That distal dual-lumen member 1720 may be constructed of heat-shrink PEBAX or another material that may be bonded (e.g., thermally by heat-shrink, with adhesive, or by some other connecting means) with the jacketing material 1708. A preferred material is nylon-PEBAX blend.

Figure 17A:
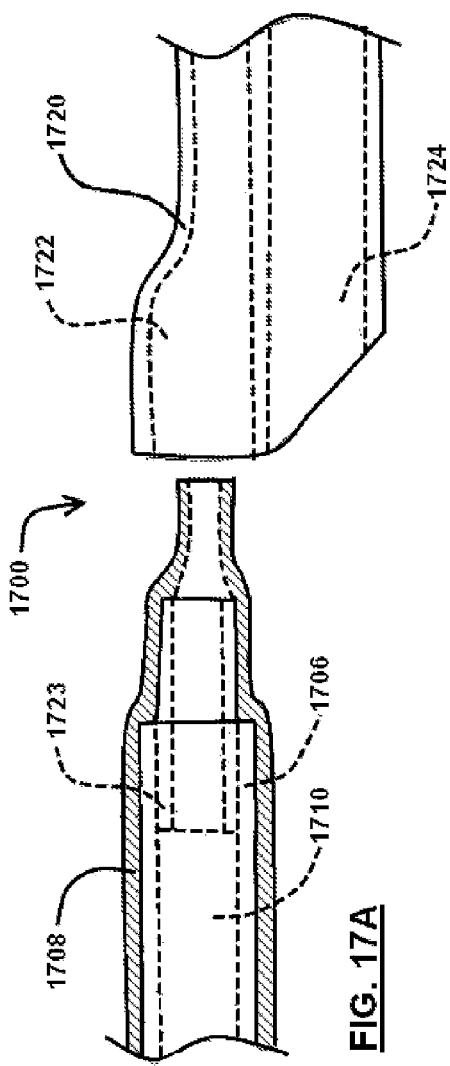
FIGS. 17A and 17B show, respectively, partially unassembled and assembled proximal and distal catheter portions of another catheter embodiment.
Figure 17B:
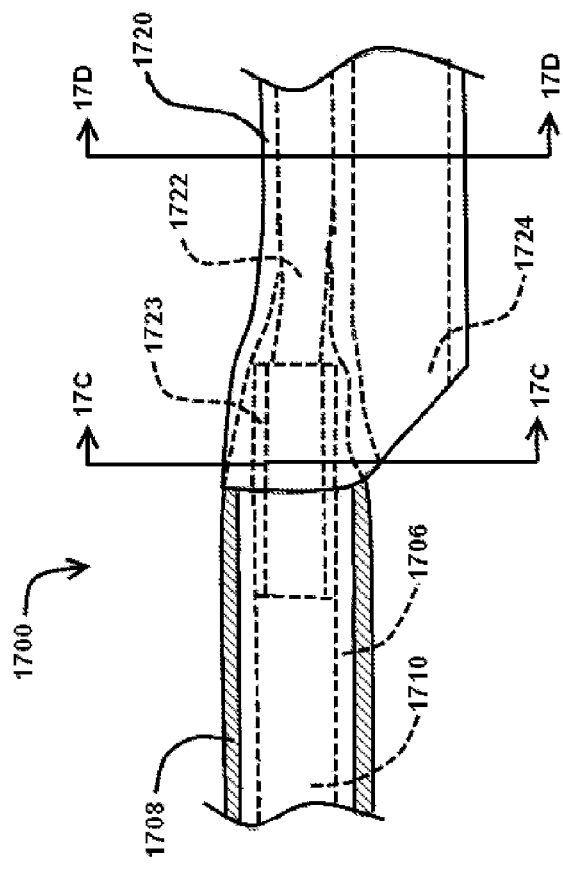

When assembling the complete catheter 1700 by inserting the distal end of the jacketed proximal portion into the upper/inflation lumen 1722 of the dual-lumen member 1720 (as shown in FIG. 17B), it may be desirable to provide a mandrel (not shown) through the proximal and distal inflation lumens 1710, 1722 so that a method step of fixedly attaching those elements (e.g., by thermoset, melt-fusing, sonic welding, applying adhesive, and/or any other method appropriate for the materials) will not occlude those lumens. A mandrel may also be provided through the wire guide lumen 1724 during assembly. As shown in FIGS. 17A-17B, the jacketing material 1708 may extend beyond the distal end of the connector tube 1723. This may help to secure the components together and provide a smooth transition between the joined inflation lumens 1710, 1722.

As shown in FIGS. 18-18C (with reference to the longitudinal section view of FIG. 17B), an assembled catheter device 1700 includes a proximal-end hub 1702 with a fitting 1704 (e.g., a Luer-type fitting for an inflation fluid source). An elongate shaft including a proximal alloy tube 1706 extends distally from the hub 1702. An intervening strain relief portion 1705 may also be provided. When embodied as a multifilar cable tube, the tube 1706 preferably will be formed as a continuous monolayer or multi-layer tube of laterally-touching coiled filars, each having a length that does not cross over itself nor other filars. This configuration will provide desirable pushability and trackability. The tubing 1706 defines a fluid-patent proximal tube lumen 1710 configured as the proximal portion of an inflation lumen that includes a distal inflation lumen portion 1722, which terminates at and is in fluid communication with a balloon lumen 1752. In some suitable configurations, filars of the multifilar tube may be swaged to create smooth inner and/or outer diameter surfaces of the tube formed thereby.

A jacketing material 1708 sealingly coats the outer surface of the cable tube 1706 and the exposed portion (outside the tube body 1706) of the thin-walled cannula 1723. The jacketing 1708 is shown in FIG. 18A, which is a transverse cross-section view of FIG. 18 along line A-A. Suitable materials for the jacketing 1708 include heat-shrink tubing such as, for example, a polyether block amide barrier material (e.g., PEBAX) that is thermoformed to the exterior of the cable tube to provide a sealing coating and maintain fluid patency of the cable tube 1706 during introduction of inflation fluid through the inflation lumen 1710. Other materials that may be used in the jacketing include HDPE, PTFE, PET, polyurethane, polyimide, polyolefin, nylon, or any combination thereof (including combinations with PEBAX).

In certain embodiments, it may be advantageous to roughen the external surface of the cable tube 1706 and/or cannula 1723 (e.g., by sanding, blasting, or any other technique that would roughen and/or otherwise increase the texture and/or surface area to enhance frictional contact between the jacketing 1708 and underlying tube and/or cannula). This roughening provides enhanced strength of attachment without affecting weight or diameter in the manner that adhesive or ancillary connectors would, while also being configured to provide the desirable trackability and pushability of these embodiments. The inner tube diameter defining the lumen 1710 may be swaged for any lengthwise portion of the tube 1706 (see, e.g., FIG. 13B). Although the texture is not visible in the drawing, one or both of the external surfaces of the cable tube 1706 and/or cannula 17233 may be roughened to enhance the connection with adjoining surfaces.

A distal portion of the elongate shaft is formed of the dual-lumen polymer shaft tube 1720 secured to the cable tube portion 1706 in the manner described above with reference to FIGS. 17A-17B, where the jacketed cannula 1723 is inserted into the distal lumen 1722. It may be advantageous to maintain a larger inner diameter functional lumen by using a mandrel or other appropriate means to expand a proximal portion of the distal lumen 1722, as shown in FIG. 17A. In this manner, the inner diameter of the cannula 1723—even though generally circular in section—will provide a path of fluid communication that is closer in size to the modified half-round distal lumen 1722 (see, e.g., FIG. 18C) than other configurations. A proximal polymer tube end preferably is attached directly to the polymer barrier coating formed by the jacketing material 1708 overlying the distal end of the cannula 1723.

In certain embodiments, it may be advantageous to roughen an external surface of that jacketing material 1708 (e.g., by any appropriate chemical and/or mechanical technique that would roughen and/or otherwise increase the texture and/or surface area to enhance frictional contact between the jacketing 1708 and the distal dual-lumen tube 1720). As described throughout this specification, any surface intended to contact and be securely fused or otherwise attached to another material may be roughened for this reason. The polymer tube 1720 preferably is formed from materials having a durometer that provides substantially similar flexibility, trackability, and pushability as the coated cable tube portion, but—in certain embodiments—the distal polymer tube portion may be more flexible than a more proximal cable tube portion. In this manner, the transition region, intermediate in the shaft length, where the coated cable tube portion ends and the polymer tube portion begins most preferably will not provide a flex point where kinking or bending is likely to occur in the manner of some prior catheter devices.

For example, a cable tube made of nitinol or stainless steel may have an outer diameter of about 20-100 mil (about 0.51-2.54 mm), with a preferred range of about 30-80 mil (about 0.76-2.03 mm) and an inner diameter about 20-70 mil (about 0.51-2.03 mm) that is less than the outer diameter. In one example, one may begin with a 12-filar stainless steel cable tube having an outer diameter of 35 mil (0.89 mm), swage it to 33 mil (0.84 mm), and provide it with a 4 mil (0.1 mm) wall liner, and a 21 mil (0.53 mm) inner diameter. The distal polymer shaft 1720 may be formed of nylon, PEBAX, a blend of nylon with PEBAX, and/or PEBAX heat-shrink (which should, for all purposes of this specification be considered as included wherever PEBAX is mentioned), polyethylene, or other suitable materials, preferably having a durometer of about 76 D, and preferably is formed as an extruded or molded dual-lumen tubing. Stated differently, the polymer tube portion provides very similar properties as compared to the cable tube portion in the region immediately adjacent the cable tube portion. This construction will provide cost savings in materials as well as providing a kink-resistant construction with desirable pushability and trackability. The transition region between the cable tube shaft portion and the distal, dual-lumen polymer tube shaft portion are illustrated with reference to FIGS. 17A and 17B, each of which is illustrated in a longitudinal partial-section view along line X-X of FIG. 18.

The distal polymer tube portion of the elongate shaft of the device 1700 is configured as a dual-lumen catheter. In this manner, the overall device 1700 includes a proximal single-lumen cable tube catheter portion 1706 and a distal dual-lumen polymer catheter portion 1720. A transverse cross-sectional view of the transition region from the single to the dual-lumen portion is shown in FIG. 18B which is a transverse cross sectional view taken along line B-B of FIG. 18 showing the jacketed cannula 1723 and distal body 1720. A fluid-patent polymer tube inflation lumen 1722 of the polymer tube 1720 sealingly encompasses the distal end of the cannula 1723. A wire guide lumen 1724 begins at an angled wire guide port 1726. A wire guide 1730 is shown extending through the wire guide lumen 1724 and the wire guide port 1726. The inflation lumen 1710 of the proximal cable tube portion of the device 1700 continues a path of fluid-patent communication into and through the distal polymer tube inflation lumen 1722, forming a continuous inflation lumen. A transverse distal cross sectional view of the polymer catheter portion 1720, distal of the single-lumen cable tube catheter portion 1706 is shown in FIG. 18C, which is taken along line C-C of FIG. 18. As shown therein, the inflation lumen portion may include a non-circular cross-section.

A balloon 1750 is secured at its proximal end to the dual-lumen catheter portion 1720. The polymer tube inflation lumen 1722 terminates where the polymer catheter portion 1720 joins the balloon 1750. The polymer tube inflation lumen 1722 is thereby in patent fluid communication with a balloon lumen 1752. A fluid-patent portion of the polymer catheter 1720 extends through the balloon lumen 1752, providing a continuation of the wire guide lumen 1724 to the distal end of the balloon 1750, which is shown with the wire guide 1730 extending therefrom. As shown in FIG. 18, radio-opaque marker bands 1735 preferably are included on or in the wire guide lumen portion of the polymer catheter 1720 that extends through the balloon lumen 1750. The marker bands 1735 preferably are oriented parallel with the ends of an intermediate expandable balloon region, such that a user can fluoroscopically determine the location of the balloon 1750 for desired deployment.

FIGS. 19A-19B show a variation of the embodiment of FIGS. 17A-18C. The thin-walled connector tube 1723 may include one or more helical/spiral scores 1729 (e.g., on internal and/or external surfaces) and/or cuts (extending through at least one wall portion) configured to enhance its flexibility and reduce the possibility of a device failure at the junction it bridges. Although shown only as extending along a distal portion of the tube 1723, the score(s) and/or cut(s) may extend over the full length and/or different portions of the connector tube. FIG. 19A shows the catheter 1700 before assembly of the proximal with the distal portion. FIG. 19B shows the assembled catheter 1700. The score 1729 is disposed in this embodiment to traverse a portion of the catheter 1700 that may need to flex at the junction of the proximal portion with the distal dual-lumen portion 1720. As in the embodiments described with reference to FIGS. 16A-18C, this embodiment will provide for efficient flow of inflation fluid.

Another embodiment of a balloon catheter 1900 is shown in FIGS. 20A-20B. FIG. 20A shows, the distal end region of a proximal cable tube 1906 covered with jacketing material 1908 (such as, for example, heat-shrinkable PEBAX). The view of FIG. 20A is a longitudinal view showing the jacket 1908 in longitudinal section, while FIG. 20B shows the jacket and the distal dual-lumen catheter portion 1920 in section view (with certain internal elements described shown in dashed lines). It preferably is sized such that its inflation lumen 1910 will provide for a flow-rate closely similar to the flow-rate provided by flow-rate-optimized half-round lumen 1922 of the distal lumen portion 1920 (particularly when a typical proximal length of the cable tube 1906 is taken into account). Rather than a short thin-walled connector tube that reduces—albeit only slightly—the inner diameter of the proximal and distal inflation lumens, a ground-down/reduced diameter distal cable tube portion 1927 is provided. Specifically, an outer diameter of a lengthwise portion at the distal end of the cable tube 1906 may be reduced by grinding, or some other appropriate mechanical, chemical, electrical, or other means. Whether the alloy tube provided is a cable tube or hypotube, the reduced-diameter portion 1927 may be scored and/or cut in the manner described with reference to FIGS. 19A-19B, such that it includes at least one cut, score, or combination thereof. The reduced diameter portion used for connecting the catheter portions while maintaining a preferred inner diameter (e.g., cannula 1723, reduced diameter tube portion 1927) collectively may be referred to as "connecting tube elements."

As shown in FIGS. 20A-20B, the reduced diameter distal cable tube portion 1927 preferably is configured/dimensioned for insertion into a proximal portion of the inflation lumen 1922 of the distal dual-lumen tube 1920 in a manner providing for efficient flow of inflation fluid therethrough. Specifically, when the catheter 1900 is assembled as shown in FIG. 20B, a patent path of fluid communication will be provided between the cable tube inflation lumen 1910 and the distal member inflation lumen 1922. The cable tube 1906 has a larger outer diameter and inner diameter in proportion to the distal member inflation lumen 1922 when compared—for example—with the embodiments shown in FIGS. 14-15. As such, in this embodiment, the inner diameters of the cable tube 1906 and the distal inflation lumen 1922 are more similar and provide for more rapid flow during inflation and/or deflation of a balloon.

The distal dual-lumen portion 1920 is shown with a wire guide lumen 1924. A distal portion of the reduced diameter distal cable tube portion 1927 may be roughened or otherwise treated to increase its surface area and/or frictional profile to improve its bonding with the jacketing material 1908. The distal dual-lumen member 1920 may be constructed of heat-shrink PEBAX, nylon/PEBAX blend, another suitable material, and/or some combination thereof that may be bonded (e.g., thermally by heat-shrink, with adhesive, or by some other connecting means) with the jacketing material 1908. The reduced diameter distal cable tube portion 1927 and the cable tube 1906 may be provided without any external jacketing material in some embodiments, and/or a lining may be provided on the inner diameter surface of its inflation lumen 1910.

When assembling the complete catheter 1900 by inserting the distal end of the jacketed proximal portion into the upper/inflation lumen 1922 of the dual-lumen member 1920, it may be desirable to provide a mandrel through the proximal and distal inflation lumens 1910, 1922 so that a method step of fixedly attaching those elements (e.g., by thermoset, melt-fusing, sonic welding, applying adhesive, and/or any other method appropriate for the materials) will not occlude those lumens. A mandrel may also be provided through the wire guide lumen 1924 during assembly. As shown in FIG. 19, the jacketing material 1908 may extend beyond the distal end of the connector tube 1923. This may help to secure the components together and provide a smooth transition between the joined inflation lumens 1910, 1922.

One example of construction is described here with reference to FIGS. 17A-18C. A cable tube 1706 is provided having an inner diameter of about 0.026 inches (about 0.66 mm) and an outer diameter of about 0.041 inches (about 1.04 mm). A cannula 1723 about 6 to about 10 mm in length is provided and fused to the inner diameter and/or distal end of the cable tube lumen 1710. The cannula may be spiral-cut as is described with reference to FIGS. 19A-19B. The fusing may be done using, for example, laser welding, soldering, or adhesive. The surfaces of the exposed portion of the cannula 1723, as well as a distal lengthwise portion of the distal and proximal ends of the cable tube 1706 are roughened. Next, a PEBAX heat-shrink jacketing is applied and head-shrunk over the entire length of the tube 1706 and cannula 1723, with about 3-4 mm extending beyond the distal cannula end in tube-like fashion with an inner diameter provided of about 0.020 inches (about 0.5 mm) to about 0.026 inches (about 0.66 mm) for the PEBAX sleeve. Although not shown, the portion of the PEBAX jacketing 1708 overlying the distal cable tube body 1706 may be trimmed to be flush with the distal cable tube end, leaving the cannula 1723 jacketed.

Next, a portion of its inflation lumen 1722 will be expanded by insertion of a mandrel (not shown; may be heated), expanding a proximal portion of its inflation lumen from about 0.021 inches (about 0.53 mm) to about 0.40 inches (about 1 mm) for a length of about 4 to about 5 mm. In this manner, a larger inner diameter "entry portion" of the distal inflation lumen 1722 will be provided to receive the cannula 1723 in a manner that provides a generally circular/cylindrical cavity without significantly reducing the overall inner diameter that will be available for fluid flow in a final assembled catheter 1700, a method that may be used with the different embodiments described herein. As such, the lumen 1722 includes an expanded inner diameter that is greater than a more distal inflation lumen portion and configured for receiving a distal multifilar tube end, a cannula, a jacketing material, or any combination thereof. Then, the jacketed cannula 1723 will be slid into the expanded portion of the distal inflation lumen 1722 (e.g., such that the distal end of the cable tube 1706 extends into the distal lumen 1722 by about 2 to about 5 mm). Mandrels (not shown) will be inserted through the inflation and wire guide lumens 1722, 1724, then the two portions will be fused together by heat-bonding, after which the material layers will be tapered to provide a smooth inner lumen as shown in FIG. 17B and a nearly constant outer diameter between the proximal and distal portions of the finished catheter 1700, although the outer diameter of the distal portion may generally be very slightly greater. FIG. 17B shows (in broken line) some differentiation of material layers, but where the distal body 1720 is fused with the jacketing 1708, the materials may be fused into essentially a single material. A balloon 1750 will be fused to the distal end of the dual-lumen portion 1720, such that the inflation lumen 1722 provides a patent path of fluid communication therewith, and a proximal hub 1702 will also be assembled to the device 1700. In preparation for use of the catheter 1700 as a medical device, the assembly may further include folding down and sterilizing the balloon.

Those of skill in the art will appreciate that other embodiments and variants of the structures and methods described above may be practiced within the scope of the present invention, and that the drawings of different embodiments are not necessarily to scale (including some figures specifically noted as not being to scale). It is therefore intended that the foregoing detailed description be regarded as illustrative rather than limiting, and that it be understood that it is the following claims, including all equivalents, that are intended to define the spirit and scope of this invention.

I claim:
1. A medical balloon catheter, comprising:
    an elongate metal alloy tube, said tube comprising;
        a proximal alloy tube end,
        a distal alloy tube end,
        a polymer barrier coating thermoformed around the alloy tube where the polymer barrier coating extends distally beyond the distal alloy tube end, an defining a fluid-patent longitudinal alloy tube lumen portion extending between the proximal and distal alloy tube ends;
    a dual-lumen polymer tube comprising:
        a proximal polymer tube end attached directly to and around the polymer barrier coating adjacent to the distal alloy tube end,
        a distal polymer tube end,
        a first lumen configured as a fluid-patent polymer tube inflation lumen that extends distally from, and is in patent fluid communication with, the longitudinal alloy tube lumen portion, and
        a second lumen configured as a wire guide lumen extending parallel to the first lumen with a wire guide port immediately adjacent to the proximal polymer tube end;
    an inflatable balloon directly attached to the distal polymer tube end such that a lumen of the balloon is in fluid communication with the first lumen;
    where the longitudinal alloy tube lumen portion and the first lumen together comprise a substantially patent path of fluid communication between the proximal alloy tube end and the balloon lumen;
    where the second lumen forms a fluid-patent path of mechanical communication for a wire guide, the second lumen configured as the wire guide lumen extended from the wire guide port immediately adjacent the proximal polymer tube end through the balloon lumen to a distal end of the balloon; and
    where the distal alloy tube end extends into a proximal portion of the first lumen and extends distally to at least a portion of the wire guide port.
2. The catheter of claim 1, where a wire guide lumen portion near the proximal polymer tube end and extending through the balloon lumen comprises at least two radio-opaque marker bands positioned to indicate an expandable region of the balloon.
3. The catheter of claim 1, where the distal alloy tube end that extends into the proximal portion of the first lumen includes a reduced outer diameter portion of the distal alloy tube end.
4. The catheter of claim 3, where the reduced outer diameter portion of the distal alloy tube end includes at least one cut, score, or combination thereof.
5. The catheter of claim 1, further comprising a tubular cannula connecting and extending into both the longitudinal alloy tube lumen portion and the first lumen.
6. The catheter of claim 5, where the tubular cannula comprises at least one cut or score configured to enhance the flexibility of the tubular cannula.
7. The catheter of claim 5, where the tubular cannula includes a spiral cut or a score configured to enhance flexibility of the tubular cannula, where a proximal portion of the polymer barrier coating includes PEBA, and a distal portion of the polymer barrier coating includes nylon.
8. The catheter of claim 1, where the direct attachment of the polymer tube to the polymer barrier coating comprises a heat-set attachment substantially fusing the two together.
9. The catheter of claim 1, where proximal-length portion of the first lumen includes an expanded inner diameter larger than an inner diameter of a distal-length portion of the first lumen such that the proximal-length portion of the first lumen is configured for receiving the distal alloy tube end, a cannula, a jacketing material, or any combination thereof.
10. The catheter of claim 1, where at least one of the alloy tube and the polymer barrier coating adjacent the distal alloy tube end includes a roughened surface configured to enhance attachment to the proximal polymer tube end.
11. The catheter of claim 1, where the alloy tube is configured as a multifilar tube that comprises stainless steel and has an outer diameter of about 20.1-100 mil and an inner diameter of about 20-80 mil.
12. The catheter of claim 1, where the alloy tube is configured as a multifilar tube that comprises stainless steel and has an outer diameter of about 30-90 mil and an inner diameter of about 20-70 mil.
13. The catheter of claim 1, where the dual-lumen polymer tube includes an inside/lumen diameter of about 21 mil for the inflation lumen and an inside/lumen diameter of about 18 mil to about 21 mil for the wire guide lumen.
14. A medical balloon catheter, comprising:
    an elongate metal alloy tube, said tube comprising;
        a proximal alloy tube end,
        a distal alloy tube end,
        a polymer barrier coating thermoformed around the alloy tube where the polymer barrier coating extends distally beyond the distal alloy tube end, and defining a fluid-patent longitudinal alloy tube lumen portion extending between the proximal and distal alloy tube ends;
    a dual-lumen polymer tube comprising:
        a proximal polymer tube end attached directly to and around the polymer barrier coating adjacent to the distal alloy tube end,
        a distal polymer tube end,
        a first lumen configured as a fluid-patent polymer tube inflation lumen that extends distally from, and is in patent fluid communication with, the longitudinal alloy tube lumen portion, and a second lumen configured as a wire guide lumen extending parallel to the first lumen with a wire guide port immediately adjacent to the proximal polymer tube end;

an inflatable balloon directly attached to the distal polymer tube end such that a lumen of the balloon is in fluid communication with the first lumen;

where the longitudinal alloy tube lumen portion and the first lumen together comprise a substantially patent path of fluid communication between the proximal alloy tube end and the balloon lumen;

where the second lumen forms a fluid-patent path of mechanical communication for a wire guide, the second lumen configured as the wire guide lumen extended from the wire guide port immediately adjacent the proximal polymer tube end through the balloon lumen to a distal end of the balloon;

where the distal alloy tube end extends into a proximal portion of the first lumen;

where the distal alloy tube end that extends into the proximal portion of the first lumen includes a reduced outer diameter portion of the distal alloy tube end, the reduced outer diameter portion defined by a tubular wall; and where the reduced outer diameter portion of the distal alloy tube end includes at least one cut, score, or combination thereof formed within the tubular wall and surrounded by the polymer barrier coating.

15. A medical balloon catheter, comprising:

an elongate metal alloy tube, said tube comprising;
 a proximal alloy tube end,
 a distal alloy tube end,
 a polymer barrier coating thermoformed around the alloy tube where the polymer barrier coating extends distally beyond the distal alloy tube end, and defining a fluid-patent longitudinal alloy tube lumen portion extending between the proximal and distal alloy tube ends;

a dual-lumen polymer tube comprising:
 a proximal polymer tube end attached directly to and around the polymer barrier coating adjacent to the distal alloy tube end,
 a distal polymer tube end,
 a first lumen configured as a fluid-patent polymer tube inflation lumen that extends distally from, and is in patent fluid communication with, the longitudinal alloy tube lumen portion, and
 a second lumen configured as a wire guide lumen extending parallel to the first lumen with a wire guide port immediately adjacent to the proximal polymer tube end;

an inflatable balloon directly attached to the distal polymer tube end such that a lumen of the balloon is in fluid communication with the first lumen;

where the longitudinal alloy tube lumen portion and the first lumen together comprise a substantially patent path of fluid communication between the proximal alloy tube end and the balloon lumen;

where the second lumen forms a fluid-patent path of mechanical communication for a wire guide, the second lumen configured as the wire guide lumen extended from the wire guide port immediately adjacent the proximal polymer tube end through the balloon lumen to a distal end of the balloon; and a tubular cannula connecting the longitudinal alloy tube lumen portion to the first lumen, where the tubular cannula extends into both the longitudinal alloy tube lumen portion and the first lumen and extends distally to a distal edge of the distal alloy tube end, and where the tubular cannula comprises at least one cut or score configured to enhance the flexibility of the tubular cannula.

* * * * *